US008331751B2

(12) United States Patent
Delaney et al.

(10) Patent No.: US 8,331,751 B2
(45) Date of Patent: Dec. 11, 2012

(54) PLANAR OPTICAL WAVEGUIDE WITH CORE OF LOW-INDEX-OF-REFRACTION INTERROGATION MEDIUM

(75) Inventors: Marie J. Delaney, Boulder, CO (US); Kevin D. Moll, Boulder, CO (US)

(73) Assignee: mBio Diagnositcs, Inc., Boulder, CO (US)

( * ) Notice: Subject to any disclaimer, the term of this patent is extended or adjusted under 35 U.S.C. 154(b) by 0 days.

(21) Appl. No.: 12/942,234

(22) Filed: Nov. 9, 2010

(65) Prior Publication Data

US 2011/0049388 A1 Mar. 3, 2011

Related U.S. Application Data

(63) Continuation-in-part of application No. 12/617,535, filed on Nov. 12, 2009, and a continuation of application No. 12/883,724, filed on Sep. 16, 2010, now abandoned.

(60) Provisional application No. 61/156,586, filed on Mar. 2, 2009.

(51) Int. Cl.
*G02B 6/10* (2006.01)
(52) U.S. Cl. ........................................ 385/129
(58) Field of Classification Search .................. None
See application file for complete search history.

(56) References Cited

U.S. PATENT DOCUMENTS

| 4,608,344 A | 8/1986 | Carter et al. |
| 4,746,179 A | 5/1988 | Dahne et al. |
| 4,810,658 A * | 3/1989 | Shanks et al. ............ 436/172 |
| 4,849,340 A | 7/1989 | Oberhardt |
| 4,852,967 A | 8/1989 | Cook et al. |
| 4,945,245 A | 7/1990 | Levin |
| 4,978,503 A | 12/1990 | Shanks et al. |
| 5,096,669 A | 3/1992 | Lauks et al. |
| 5,120,131 A * | 6/1992 | Lukosz ..................... 356/481 |
| 5,166,515 A * | 11/1992 | Attridge .................. 250/227.25 |
| 5,227,134 A | 7/1993 | Janata |
| 5,344,784 A | 9/1994 | Attridge |

(Continued)

FOREIGN PATENT DOCUMENTS
AU  768800  9/2001
(Continued)

OTHER PUBLICATIONS

Schmidt, O., et al., "Fluorescence Spectrometer-on-a-Fluidic-Chip", "Lab on a Chip", 2007, pp. 626-629, vol. 7, Publisher: The Royal Society of Chemistry.

(Continued)

*Primary Examiner* — Sung Pak
(74) *Attorney, Agent, or Firm* — Lathrop & Gage LLP

(57) ABSTRACT

An apparatus for illuminating a sample includes a planar waveguide. The planar waveguide includes a first substrate, including a first outer surface and a first inner surface, and a second substrate, including a second outer surface and a second inner surface. The first and second inner surfaces of the first and second substrates, respectively, are spaced apart from each other and partly define a volume for confining the sample therein. The apparatus also includes a light source for providing light directed toward the planar waveguide, such that the light is optically coupled to and contained within the planar waveguide between the outer surfaces of the first and second substrates, while illuminating at least a portion of the sample confined within the volume.

29 Claims, 14 Drawing Sheets

U.S. PATENT DOCUMENTS

| | | | |
|---|---|---|---|
| 5,348,859 | A | 9/1994 | Brunhouse et al. |
| 5,437,840 | A | 8/1995 | King et al. |
| 5,469,264 | A * | 11/1995 | Shigemori .................... 356/417 |
| 5,496,700 | A | 3/1996 | Ligler et al. |
| 5,599,668 | A | 2/1997 | Stimpson et al. |
| 5,633,724 | A | 5/1997 | King et al. |
| 5,677,196 | A * | 10/1997 | Herron et al. ................. 436/518 |
| 5,747,274 | A | 5/1998 | Jackowski |
| 5,766,957 | A * | 6/1998 | Robinson et al. ............ 436/165 |
| 5,832,165 | A | 11/1998 | Reichert et al. |
| 5,843,651 | A | 12/1998 | Stimpson et al. |
| 5,846,842 | A * | 12/1998 | Herron et al. ................. 436/518 |
| 5,858,800 | A * | 1/1999 | Shigemori et al. ........... 436/518 |
| 5,919,712 | A * | 7/1999 | Herron et al. ................. 436/518 |
| 5,959,292 | A | 9/1999 | Duveneck et al. |
| 5,962,238 | A | 10/1999 | Sizto et al. |
| D426,783 | S | 6/2000 | Christensen et al. |
| 6,108,463 | A | 8/2000 | Herron et al. |
| 6,137,117 | A | 10/2000 | Feldstein et al. |
| 6,192,168 | B1 * | 2/2001 | Feldstein et al. ................ 385/12 |
| 6,222,619 | B1 | 4/2001 | Herron et al. |
| 6,242,267 | B1 | 6/2001 | Herron et al. |
| 6,246,825 | B1 | 6/2001 | Kershaw |
| 6,287,871 | B1 | 9/2001 | Herron et al. |
| 6,316,274 | B1 | 11/2001 | Herron et al. |
| 6,356,676 | B1 | 3/2002 | Herron et al. |
| 6,384,912 | B2 | 5/2002 | Kraus et al. |
| 6,395,558 | B1 | 5/2002 | Duveneck et al. |
| 6,485,905 | B2 | 11/2002 | Hefti |
| 6,574,390 | B2 | 6/2003 | Kropp |
| 6,596,545 | B1 | 7/2003 | Wagner et al. |
| 6,611,634 | B2 * | 8/2003 | Herron et al. .................... 385/12 |
| 6,682,942 | B1 | 1/2004 | Wagner et al. |
| 6,686,208 | B2 | 2/2004 | Meusel et al. |
| 6,767,733 | B1 | 7/2004 | Green |
| 6,847,746 | B2 | 1/2005 | Uchiyama |
| 6,861,251 | B2 | 3/2005 | Green |
| 6,951,715 | B2 | 10/2005 | Cunningham et al. |
| 6,954,580 | B2 | 10/2005 | Soskind et al. |
| 6,961,490 | B2 | 11/2005 | Maisenhoelder et al. |
| 6,979,567 | B2 * | 12/2005 | Herron et al. ............... 435/287.1 |
| 6,984,491 | B2 | 1/2006 | Mirkin et al. |
| 7,022,515 | B2 | 4/2006 | Herron et al. |
| 7,056,676 | B2 | 6/2006 | Korlach et al. |
| 7,145,645 | B2 | 12/2006 | Blumenfeld et al. |
| 7,175,811 | B2 * | 2/2007 | Bach et al. ................. 422/82.11 |
| 7,189,361 | B2 | 3/2007 | Carson et al. |
| 7,202,076 | B2 | 4/2007 | Cunningham et al. |
| 7,236,666 | B2 | 6/2007 | Towle et al. |
| 7,248,361 | B2 | 7/2007 | Kiesel et al. |
| RE39,772 | E | 8/2007 | Herron et al. |
| 7,268,868 | B2 | 9/2007 | Kiesel et al. |
| 7,276,368 | B2 | 10/2007 | Saaski |
| 7,327,454 | B2 | 2/2008 | Cunningham et al. |
| 7,368,281 | B2 | 5/2008 | Mozdy et al. |
| 7,386,199 | B2 | 6/2008 | Schmidt et al. |
| 7,456,953 | B2 | 11/2008 | Schmidt et al. |
| 7,474,777 | B2 | 1/2009 | Kirsch et al. |
| 7,496,245 | B2 | 2/2009 | Saaski |
| 7,522,811 | B2 | 4/2009 | Schmidt et al. |
| 7,529,438 | B2 | 5/2009 | Schmidt et al. |
| 7,781,226 | B2 | 8/2010 | McDevitt et al. |
| 2005/0036728 | A1 | 2/2005 | Braunisch |
| 2006/0024756 | A1 | 2/2006 | Tibbe et al. |
| 2006/0068412 | A1 | 3/2006 | Tang |
| 2006/0188873 | A1 | 8/2006 | Abel et al. |
| 2007/0189668 | A1 * | 8/2007 | Payne ............................. 385/33 |
| 2007/0207513 | A1 | 9/2007 | Sorensen et al. |
| 2007/0299327 | A1 | 12/2007 | Georgakoudi et al. |
| 2008/0219616 | A1 | 9/2008 | Wimberger-Friedl et al. |
| 2009/0014360 | A1 | 1/2009 | Toner et al. |
| 2009/0079963 | A1 | 3/2009 | Ermantraut et al. |
| 2009/0159442 | A1 | 6/2009 | Collier et al. |
| 2009/0215072 | A1 | 8/2009 | McDevitt et al. |
| 2009/0325192 | A1 | 12/2009 | Kirakossian et al. |
| 2010/0220318 | A1 | 9/2010 | Moll et al. |
| 2010/0291588 | A1 | 11/2010 | McDevitt et al. |

FOREIGN PATENT DOCUMENTS

| | | |
|---|---|---|
| CA | 2069539 A1 | 12/1992 |
| CA | 2162996 | 11/1994 |
| CA | 2248189 | 9/1997 |
| CA | 2303794 | 3/1999 |
| EP | 0519623 B1 | 8/1998 |
| EP | 0700514 B1 | 11/2001 |

OTHER PUBLICATIONS

Singh, K., et al., "Analysis of Cellular Structure by Light Scattering Measurements in a New Cytometer Design Based on a Liquid-Core Waveguide", "IEE Proc.-Nanobiotechnol.", Feb. 2004, pp. 10-16, vol. 151, No. 1, Publisher: IEE.

Axelrod, D., "Cell-Substrate Contacts Illuminated by Total Internal Reflection Fluorescence", "The Journal of Cell Biology", Apr. 1, 1981, pp. 141-145, vol. 89, Number Apr. 1981, Publisher: The Rockefeller University Press.

Axelrod, D., "Total Internal Reflection Fluorescence Microscopy in Cell Biology", "Traffic 2001", Nov. 2001, pp. 764-774, vol. 2, No. 11, Publisher: Munksgaard International Publishers.

Desmat, T., et al., "Nonthermal Plasma Technology as a Versatile Strategy for Polymeric Biomaterials Surface Modification: A Review", "BioMacromolecules", Sep. 2009, p. 28, vol. 10, No. 9, Publisher: American Chemical Society, Published in: US.

Duveneck, G.L., et al., "Planar Waveguides for Ultra-High Sensitivity of the Analysis of Nucleic Acids", "Analytica Chimica Acta", 2002, pp. 49-61, vol. 469, Publisher: Elsevier Science B.V.

Golden, J.P., et al., "A Comparison of Imaging Methods for use in an Array Biosensor", "Biosensors and Bioelectronics", 2002, pp. 719-725, vol. 17, Publisher: Elsevier Science B.V.

Grandin, H.M., et al., "Waveguide Excitation Fluorescence Microscopy: A New Tool for Sensing and Imaging the Biointerface", "Biosensors and Bioelectronics", 2006, pp. 1476-1482, vol. 21, Publisher: Elsevier B.V.

Herron, J.N., et al., "Fluorescent Immunosensors Using Planar Waveguides", "Advances in Fluorenscence Sensing Technology", 1993, pp. 28-39, vol. 1885, Publisher: SPIE, Published in: US.

Ligler, F.S., et al., "Array Biosensor for Detection of Toxins", "Analytical and Bioanalytical Chemistry", Jun. 13, 2003, pp. 469-477, vol. 377, Publisher: Springer-Verlag.

Ligler, F.S., et al., "Integrating Waveguide Biosensor", "Analytical Chemistry", Feb. 1, 2002, pp. 713-719, vol. 74, No. 3, Publisher: American Chemical Society.

Liron, Z., et al., "Voltage-Induced Inhibition of Antigen-Antibody Binding at Conducting Optical Waveguides", "Biosensors and Bioelectronics", 2002, pp. 489-494, vol. 17, Publisher: Elsevier Science B.V.

Lundgren, J.S., et al., "A Liquid Crystal Pixel Array for Signal Discrimination in Array Biosensors", "Biosensors and Bioelctronics", 2000, pp. 417-421, vol. 15, Publisher: Elsevier Science S.A.

Myers, F.B., et al., "Innovations in Optical Microfluidic Technologies for Point-of-Care Diagnostics", "Lab on a Chip", Oct. 30, 2008, pp. 2015-2031, vol. 8, Publisher: The Royal Society of Chemistry.

O'Brien, T., et al., "The Development of Immunoassays to Four Biological Threat Agents in a Bidiffractive Grating Biosensor", "Biosensors and Bioelectronics", 2000, pp. 815-828, vol. 14, Publisher: Elsevier Science S.A.

Okagbare, P.I., et al., "Fabrication of a Cyclic Olefin Copolymer Planar Waveguide Embedded in a Multi-Channel Poly Fluidic Chip for Evanescence", "Lab on a Chip", Nov. 4, 2009, pp. 66-73, vol. 10, Publisher: The Royal Society of Chemistry.

Young, Lee W., "Notification of Transmittal of the International Search Report/Written Opinion of the International Searching Authority re PCT/US10/25172", Nov. 8, 2010, Published in: PCT.

Risk, W.P., et al., "Optical Waveguides with an Aqueous Core and a Low-Index Nanoporous Cladding", "Optics Express", Dec. 27, 2004, pp. 6446-6455, vol. 12, No. 26, Publisher: Optical Society of America.

Rowe-Taitt, C., et al., "Evanescent Wave Fluorescence Biosensors", "Biosensors and Bioelctronics", 2005, pp. 2470-2487, vol. 20, Publisher: Elsevier B.V.

Schmidt, H., et al., "Integrated Optical Waveguides with Liquid Cores", "Applied Physics Letters", Oct. 2004, pp. 3477-3479, vol. 85, No. 16, Publisher: American Institute of Physics.

Schmidt, H., et al., "Integrated Optofluidic Chips for Single Molecule Analysis", "Presentation", Jan. 24, 2008, p. 29, Publisher: University of California, Santa Cruz, Applied Optics Group.

Schmidt, H., et al., "Optofluidic Waveguides: I. Concepts and Implementations", "Microfluid Nanofluid", 2008, pp. 3-16, vol. 4, Publisher: Springer-Verlag.

Schmidt, H., et al, "Integrated Arrow Waveguides with Hollow Cores", "Optics Express", Jun. 14, 2004, pp. 2710-2715, vol. 12, No. 12, Publisher: Optical Society of America.

Schmidt, H., et al., "Researchers Guide Light Through Liquids and Gases on a Chip, a Major Step Forward for Optical Sensing Technology", "Press Release", Oct. 18, 2004, p. 3 vol. 831, Publisher: University of California Santa Cruz.

Schueller, O., et al., "Fabrication of Liquid-Core Waveguides by Soft Lithography", "Advanced Materials", 1999, pp. 37-41, vol. 11, No. 1, Publisher: Wiley-VCH Verlag GmbH.

TIRF Technologies, "Shallow Angle Fluorescence Microscopy", Nov. 10, 2010, p. 1 Publisher: TIRF Technologies, Inc.

* cited by examiner

PLANAR OPTICAL WAVEGUIDE WITH CORE OF LOW-INDEX-OF-REFRACTION INTERROGATION MEDIUM

CROSS REFERENCE TO RELATED APPLICATIONS

The present application is a Continuation of U.S. patent application Ser. No. 12/883,724, filed on Sep. 16, 2010, entitled PLANAR OPTICAL WAVEGUIDE WITH CORE OF LOW-INDEX-OF-REFRACTION INTERROGATION MEDIUM, which is a Continuation-in-Part of U.S. patent application Ser. No. 12/617,535, filed on Nov. 12, 2009, entitled WAVEGUIDE WITH INTEGRATED LENS, which claims priority to U.S. Provisional Patent Application Ser. No. 61/156,586, filed on Mar. 2, 2009, entitled WAVEGUIDE WITH INTEGRATED LENS, all of which are incorporated by reference in their entireties into the present application.

GOVERNMENT INTEREST

This research was funded in part by government support under the U.S. Department of Commerce National Institute of Standards (NIST) Advanced Technology Program (ATP), award number 70NANB7H7053. The Government has certain rights in this invention.

BACKGROUND

Fluorescently labeled probes provide a convenient method of characterizing the content of biological samples. By tailoring the binding chemistry of a fluorescent probe, high specificity can be achieved for detection of complex molecules such as RNA, DNA, proteins, and cellular structures. Since fluorophores typically absorb and re-emit Stokes-shifted radiation regardless of being bound or unbound to a species to be detected, the bound and unbound fluorophores must be separated.

One common method to separate the bound fluorophores from the unbound fluorophores relies on spatial localization of the fluorescently labeled species. For example, in a 'sandwich immunoassay,' a surface is chemically treated to bind a species to be detected to that surface. The fluorescent probes then attach to the species that are bound to the surface. Unbound fluorophores can then be removed from the system with a wash step.

Background fluorescence can be further reduced if the excitation light can be confined to the surface. Total internal reflection fluorescence (TIRF) is one method of reducing background fluorescence. In general, when light propagates from one medium to another, a portion of the light will be reflected at the interface. If the light is propagating into a material with a lower index of optical refraction, however, all of the light will be reflected if the angle at which the beam is incident on the surface is greater than the 'critical angle' (relative to the surface normal). In the lower index material, the light intensity exponentially decays with distance from the surface. This exponentially decaying field (known as an 'evanescent field') has a characteristic decay length on the order of 100 nanometers to 1 micrometer for visible light. The light of the evanescent field will, therefore, only excite fluorophores that are localized at the surface.

In a simplified implementation, TIRF is performed with a laser beam reflecting once from the surface. This is the basis of well established TIRF microscopy and other biosensing techniques. By confining the laser beam inside a waveguide, however, multiple reflections can be realized and larger areas can be illuminated. Several waveguide geometries are possible, each having certain tradeoffs.

Single-mode planar waveguides, also called thin film waveguides or integrated optical waveguides, confine light into a small cross sectional area with the thin dimension smaller than the wavelength of propagating light. The advantage of single-mode waveguides is that significantly stronger evanescent fields are generated. A disadvantage of single-mode waveguides is that for efficient light coupling, they typically require a prism or grating with precise alignment tolerances. In addition, single-mode planar waveguides are expensive to manufacture because the guiding layer is typically a thin-film with strict thickness tolerances deposited on a substrate. In contrast, a multimode planar waveguide is substantially easier to couple a laser beam to and simpler to construct than single-mode planar waveguides. For example, a standard 1 millimeter thick microscope slide makes an effective waveguide into which light can be coupled through the edge of the slide. Additionally, dimensions for multimode waveguides are compatible with current plastic injection-molding techniques.

For a fluorescence-based assay system, a uniform evanescent field is desired in the detection region. By definition, the strength of the evanescent field is uniform along the direction of light propagation for a single-mode planar waveguide (neglecting scattering losses and absorption inside the waveguide). For a disposable clinical device, however, cost, robustness, and ease of use are of similar importance. By adjusting input coupling to a multimode waveguide, uniformity and field strength of the evanescent field can be optimized.

While each individual mode in a multimode waveguide has a uniform intensity along the direction of propagation, a distribution of modes will be excited when coupling to a multimode waveguide; this distribution of modes will constructively and destructively interfere on the surface and lead to a spatially varying field strength. When the thickness of the waveguide is much larger than the wavelength of light, the mode structure of the waveguide can be neglected, and the intensity in the waveguide can be treated as a conventional diffracting beam that totally-internally reflects from the two surfaces of the waveguide and interferes with neighboring reflections.

FIG. 1 illustrates several examples of existing coupling schemes 105-115 involving multimode waveguides. Coupling scheme 105 using a multimode waveguide 120 involves focusing a laser beam 125 that propagates parallel to a waveguide 120 into the edge of waveguide 120 with a cylindrical lens 130. The field strength of a total internal reflection ("TIR") beam, however, is maximized for a beam that is incident at the critical angle and zero for a beam with an incident angle 90° from the surface normal (i.e., grazing incidence). Thus, an incident beam that is parallel to the TIR surface will have small evanescent field strength when coupled to waveguide 120 with cylindrical lens 130 in the configuration of the scheme 105.

A variation on coupling scheme 105 is illustrated by coupling scheme 110. In coupling scheme 110, a laser beam 135 focused by a cylindrical lens 140 is incident on the edge of a waveguide 145 with an appropriate angle such that a central ray of laser beam 135 inside the waveguide impinges on the surface near the critical angle for TIR to maximize the evanescent field strength. A compromise between field strength and uniformity may be made by the choice of focusing optics. If a nearly collimated beam is used to achieve high field intensity by operating near the critical angle for TIR, the beam must make many reflections within the waveguide before the surface intensity becomes sufficiently uniform, thus requiring a longer waveguide. If the beam is highly focused, however, then the surface intensity normalizes in very few reflections, but a significant amount of power is contained in rays propagating outside the critical angle and leads to reduced evanescent field strength down the length of the waveguide.

Precise alignment of a cylindrical lens, such as lenses 130 and 140, relative to the input face of a waveguide, such as waveguides 120 and 145, respectively, must be made in order to have a laser beam focused on the input face. One proposed solution to this problem is illustrated by a coupling scheme 115. In coupling scheme 115, a lens 150 is incorporated with a waveguide 155 as a single optical component, made, for example, by bonding the lens element to the planar waveguide or by molding a single optical component. While this allows the focus of lens 150 to be precisely distanced from the edge of waveguide 155, careful alignment of a laser beam 160 relative to lens 150 of waveguide 155 must still be made to couple beam 160 to waveguide 155. For applications requiring repeated placement of a waveguide component relative to the light source, it is highly desirable for the light coupling to be relatively insensitive to misalignment.

In practical applications, the penetration depth of the evanescent field usually is less than a wavelength of the incident light. This aspect is an advantage in some applications, as the evanescent field can serve as a mechanism to illuminate only a volume of interest, e.g., a thin layer in the lower refractive index medium proximate to the waveguide surface. On the other hand, when the object of interest, such as a cell or the bulk of a solution, extends substantially beyond the penetration depth of the evanescent wave, evanescent illumination can be less effective than floodlight-type illumination.

A subfield of integrated optofluidics is concerned with the development of methods for using optical waveguides to illuminate extended liquid media. Most of the developed methods involve the containment of a liquid sample by other liquid and/or solid materials, thereby effectively creating a waveguide for illuminating the liquid sample. Most TIR-based designs involve surrounding the liquid sample with media of lower index of refraction than that of the liquid sample itself. It is then theoretically possible for light to be guided in the liquid sample by TIR at the interface between the high refractive index liquid and the lower refractive index surroundings. However, in practice, waveguiding in a liquid sample contained in another material is difficult due to the fact that common liquids have lower refractive indices than common solids; for example, water has a refractive index of approximately 1.33, while most solid materials have an index of refraction of 1.4 or more. Consequently, a majority of the TIR waveguide designs involve using either high refractive index (i.e., "high-n") liquids or more exotic low refractive index (i.e., "low-n") solids.

In interference-based optofluidic waveguides, light is confined to a liquid core by reflection from surrounding materials including two or more layers of higher-index materials combined to result in a lower effective refractive index for the surrounding media. Some interference-based optofluidic waveguides include photonic crystals, such as multiple alternating layers of materials of different indices of refraction

SUMMARY OF THE CLAIMED INVENTION

Embodiments disclosed below allow light to be coupled to a planar waveguide providing a strong evanescent field for sample illumination, while eliminating or greatly reducing inadvertent misalignment by a user. The various embodiments further allow facile tuning of the internal propagation angle inside the waveguide, providing simple adjustment of evanescent field strength. Another embodiment also provides apparatus for performing assays involving placement of a fluidic chamber on a planar waveguide in a manner that is insensitive to the optical properties of the chamber.

In an embodiment, apparatus for illuminating a sample for analysis is disclosed. The apparatus includes a light source, a planar waveguide, and a refractive volume. The light source provides light along a propagation vector. The planar waveguide is oriented such that the propagation vector is perpendicular to the normal vector of the planar waveguide and offset from the planar waveguide in a direction parallel to the normal vector of the planar waveguide. The refractive volume, which is positioned proximate to the planar waveguide, optically couples light provided by the light source to the planar waveguide.

Another embodiment sets forth a method for performing sample analysis. Light is provided from a light source along a propagation vector. A refractive volume positioned proximate to a planar waveguide is illuminated with the light. The waveguide is oriented such that the propagation vector is perpendicular to the normal vector of the planar waveguide and offset from the planar waveguide in a direction parallel to the normal vector of the planar waveguide. The light is then coupled to the planar waveguide via the refractive volume.

Apparatus for performing biological assays is disclosed in yet another embodiment. The apparatus includes a light source, a planar waveguide, a refractive volume, and a detector. The light source provides light along a propagation vector. The planar waveguide has a plurality of specific binding molecules bound to a face thereof. The planar waveguide could further have an array of two or more dissimilar specific binding molecules bound to the face thereof. Additionally, the optical axis of the planar waveguide is oriented parallel to the propagation vector and offset from the propagation vector in a direction perpendicular to a face of the planar waveguide. The refractive volume optically couples light provided by the light source to the planar waveguide and is positioned proximate to the planar waveguide. The refractive volume includes at least a section of a plano-convex cylindrical lens. The detector is positioned to detect light emitted from a region proximate to the face of the planar waveguide having the plurality of specific binding molecules bound thereto.

In an embodiment, an apparatus for illuminating a sample includes a planar waveguide. The planar waveguide includes a first substrate, with a first outer surface and a first inner surface, and a second substrate, with a second outer surface and a second inner surface. The first and second inner surfaces of the first and second substrates, respectively, are spaced apart from each other and partly define a volume for confining the sample therein. The apparatus further includes a light source for providing light directed toward the planar waveguide such that the light is optically coupled to and contained within the planar waveguide between the outer surfaces of the first and second substrates, while illuminating at least a portion of the sample contained within the volume.

In a further embodiment, the sample contains at least one object, and the planar waveguide and the light source are configured to cooperate to uniformly illuminate the object. In a still further embodiment, the object is greater than one micrometer in diameter.

In a yet further embodiment, the apparatus further includes a gasket for separating the first and second inner surfaces of the first and second substrates, respectively, while further defining the volume for confining the sample therein. In a further embodiment, the light is contained between the outer surfaces of the first and second substrates at least in part by total internal reflection. In a still further embodiment, the light source provides uncollimated light.

In another embodiment, a sample analysis system includes a planar waveguide. The planar waveguide in turn includes a first substrate, with a first outer surface and a first inner surface, and a second substrate, with a second outer surface and a second inner surface. The first and second inner surfaces of the first and second substrates, respectively, are spaced apart from each other and partly define a volume for confining a sample therein. The sample analysis system further includes a first light source for providing a first illumination directed toward the planar waveguide. The first illumination is optically coupled to and contained within the planar waveguide between the outer surfaces of the first and second substrates while illuminating at least a portion of the sample confined within the volume. The sample analysis system also includes a detector for detecting a first light signal emitted from the sample as a result of the first illumination interacting with the portion of the sample.

In a further embodiment, the sample analysis system includes a second light source, which is configured for providing a second illumination, and imaging optics for directing the second illumination from the second light source to at least another portion of the sample and to the detector. The detector is further configured for detecting a second light signal resulting from the second illumination interacting with the at least another portion of the sample.

BRIEF DESCRIPTION OF THE FIGURES

FIGS. 12 and 13 show collimated light propagating through thick and thin waveguides. FIGS. 14 and 15 show diverging light in thick and thin waveguides. In all figures, partial reflections at various internal interfaces (e.g., the substrate-to-interrogation medium interface) have been omitted for clarity.

Figure 1:
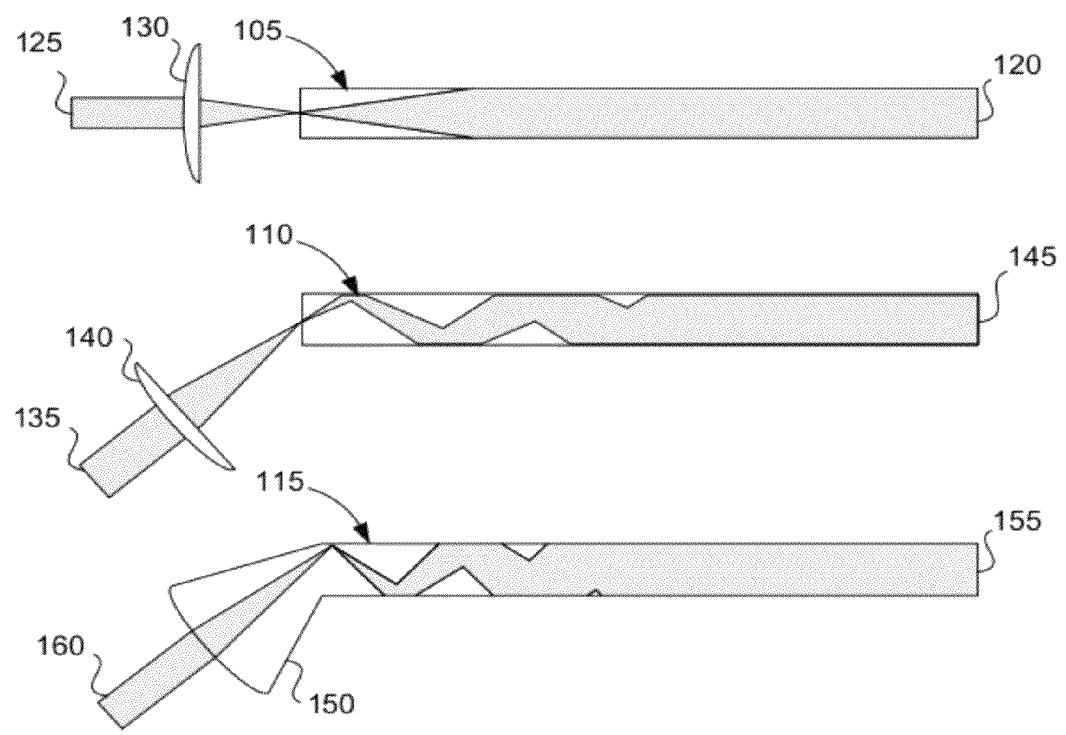
FIG. 1 illustrates several examples of existing coupling schemes involving multimode waveguides.

It is noted that, for purposes of illustrative clarity, certain elements in the drawings may not be drawn to scale.

DETAILED DESCRIPTION

Embodiments of the present technology provide for sample illumination such as that involved in fluorescence detection and assay based on evanescent fields using apparatus including a waveguide with an integrated lens. The overall configuration of the apparatus may be such that fluorescence-emitting molecules bound to a waveguide surface are excited by an evanescent field penetrating into the adjacent solution from a light beam propagated within the waveguide, the propagated beam being introduced by an integrally connected lens. The collimated beam of light such as a laser beam may propagate parallel to the waveguide surface such that the system is insensitive to translation of the waveguide. The incident beam may be also appropriately offset from the optical axis of the waveguide such that refraction of the light at the lens surface directs the beam into the waveguide at an angle close to the critical angle for TIR. Additionally, a second integrated cylindrical lens may be added to the output end of the waveguide. This addition of the second integrated cylindrical lens may facilitate a second laser being coupled in the opposite direction, such as for use in multi-color fluorescence assays.

The apparatus may also allow a fluidic chamber to be bound to the planar waveguide such that the chamber contact with the planar waveguide is outside the optical path of the propagating light, eliminating restrictions on optical properties of material comprising the chamber. In some previous configurations, fluidic chambers have utilized low index of refraction materials in contact with the planar waveguide with mechanical clamping in order to limit optical losses at the waveguide/chamber contact area. By separating the waveguide/chamber contact from the optical path, traditional bonding methods such as adhesives or plastic welding may be used to attach the chamber to the waveguide. Moreover, the fluidic chamber may include or be formed in part by a second planar waveguide, wherein the fluidic chamber is disposed between two planar waveguides. In such an arrangement light may be coupled to both planar waveguides as well as the volume formed by the fluidic chamber.

Figure 2:
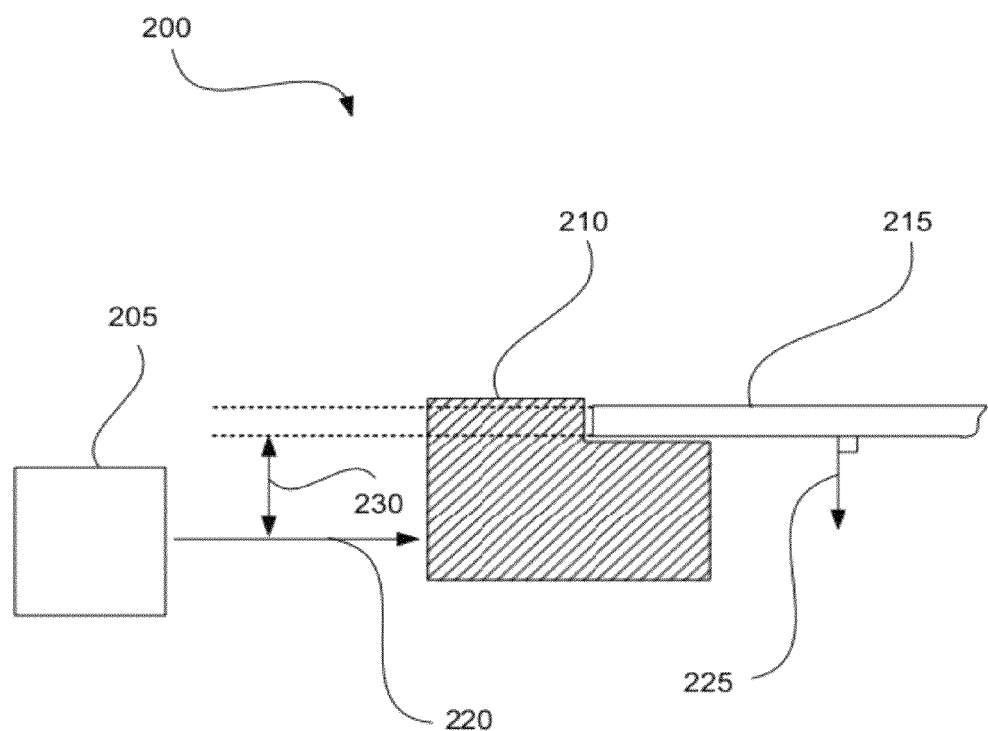
FIG. 2 illustrates a generalized configuration descriptive of exemplary embodiments.

FIG. 2 illustrates a generalized configuration 200 descriptive of exemplary embodiments. Configuration 200 includes a light source 205, a refractive volume 210, and a planar waveguide 215. Light source 205 can include a laser or any other source of collimated or near-collimated light that provides light along a propagation vector 220. Refractive volume 210 is positioned proximate to planar waveguide 215. Refractive volume 210 and planar waveguide 215 may lack a discontinuity in index of refraction therebetween. For example, refractive volume 210 may be adjacent to or abutted to waveguide 215 with an index matching fluid (not shown) occupying any gap therebetween. Alternatively, refractive volume 110 may be integrated with planar waveguide 215 as a single unit or article. Planar waveguide 215 is oriented such that propagation vector 220 is perpendicular to normal vector 225 of planar waveguide 215. Furthermore, planar waveguide 215 has an offset 230 in a direction parallel to the normal vector 225 of planar waveguide 215.

Figure 3:
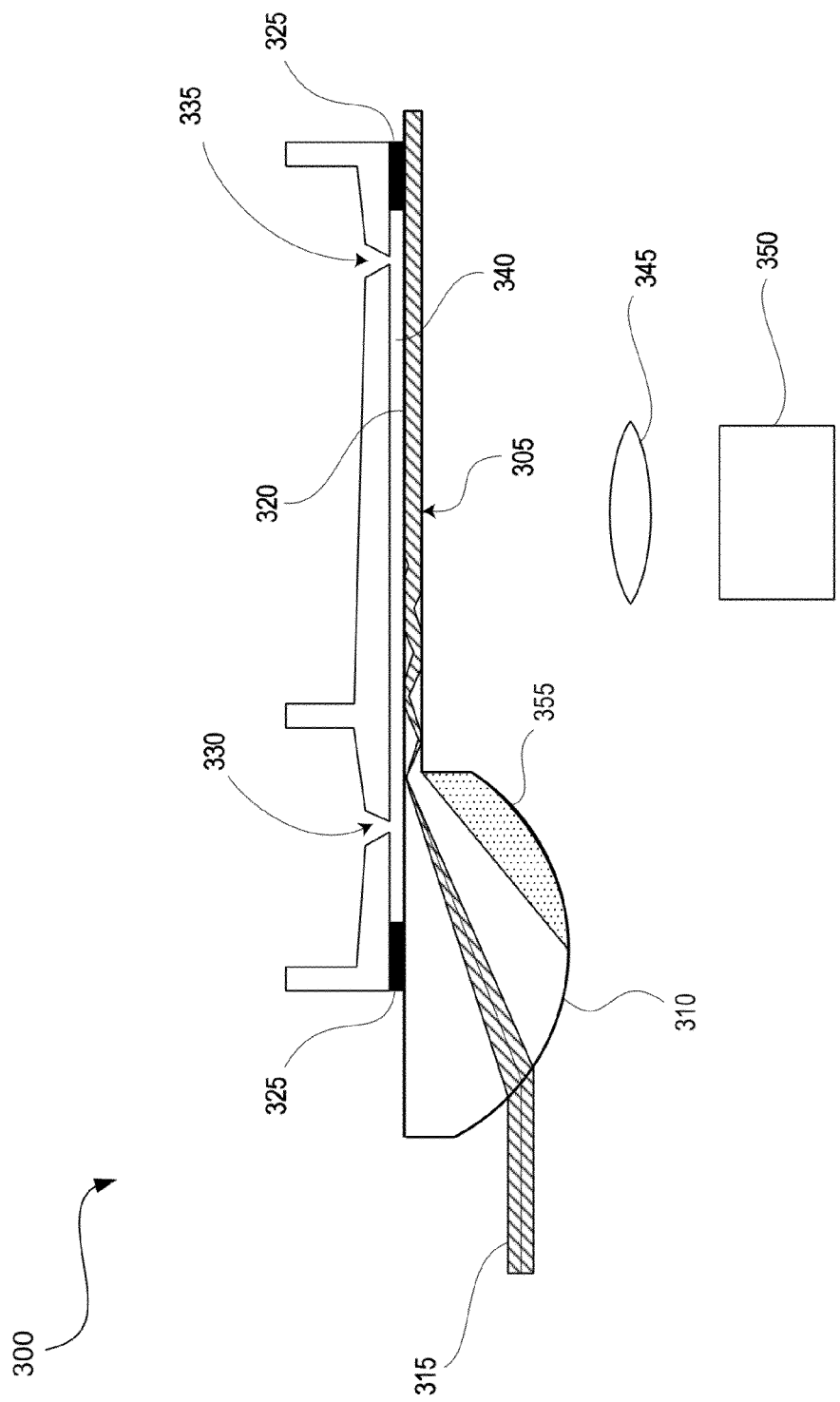
FIG. 3 illustrates a cross-sectional view of an exemplary waveguide with an integrated lens.

FIG. 3 illustrates an exemplary cross-sectional view 300 of a waveguide 305 with an integrated lens 310 according to one embodiment. Additionally, view 300 depicts a collimated light beam 315 such as that of a laser with a wavelength appropriate to excite fluorescent probes at an assay surface 320. Planar waveguide 305 with integrated lens 310 is configured to inject collimated light beam 315 through a bottom surface of planar waveguide 305. A flowcell is formed from a sealing mechanism, such as a gasket 325, an inlet port 330, an output port 335, and a fluidic sample chamber 340, in which chemical compounds deposited on assay surface 320 of waveguide 305 may bind the desired target compound to the surface. Collection and filtering optics 345 can capture fluorescence from assay surface 320 of waveguide 305. A signal corresponding to the fluorescence so captured may then be directed to an imaging device 350 such as a CCD or CMOS camera. Furthermore, the roof, the floor, and/or the walls of the flow cell may be used as a surface on which compounds are deposited.

It is noteworthy that fluidic sample chamber 340 may include or be formed in part by a second planar waveguide, similar to waveguide 305, such that fluidic sample chamber 340 is disposed between two planar waveguides. In such a configuration, light may be coupled to both waveguide 305 and the second planar waveguide as well as the volume formed by the fluidic sample chamber 340. The principles described herein are similarly applicable to configurations having multiple planar waveguides.

Figure 4:
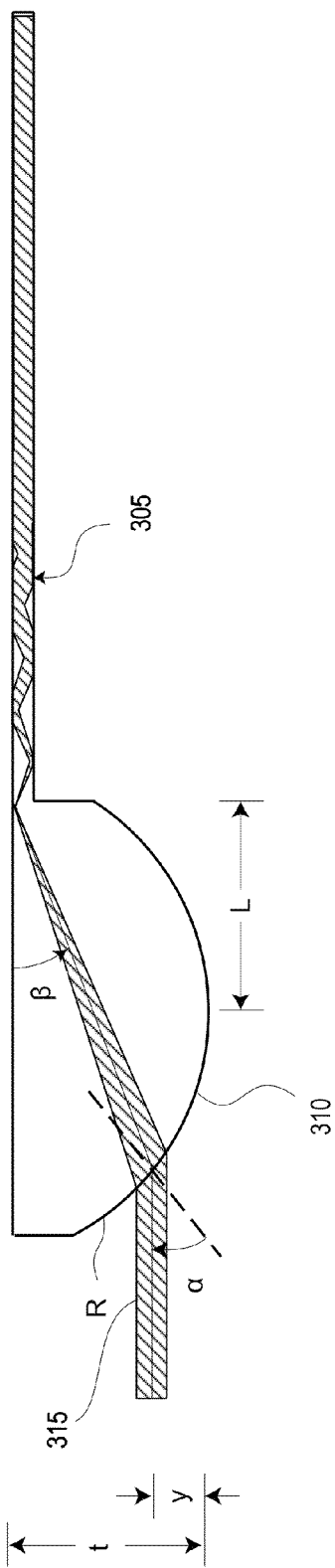
FIG. 4 provides a detailed cross-sectional view of the waveguide with the integrated lens depicted in FIG. 3.
Figure 5:
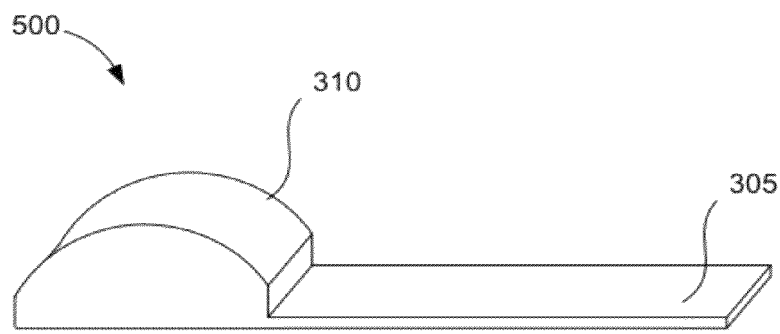
FIG. 5 is a cavalier projection view illustrating the exemplary waveguide with the integrated lens.

FIG. 4 provides a detailed cross-sectional view 400 of waveguide 305 with integrated lens 310. For further reference, FIG. 5 is a cavalier projection view 500 illustrating waveguide 305 with integrated lens 310. Referring back to FIG. 4, collimated light beam 315 propagates in a direction parallel or nearly parallel to the optical axis of waveguide 305, but offset from the optical axis such that it strikes the curved surface of integrated lens 310. For a clinical instrument in which the waveguide structure is a removable consumable item, this geometry may loosen the positional tolerances necessary to couple collimated light beam 315 reproducibly to waveguide 305. Collimated light beam 315 impinges on the curved surface of integrated lens 310 at a non-zero angle α relative to the local surface normal of integrated lens 310, as illustrated in FIG. 4.

As a result of refraction explained by Snell's law, collimated light beam 315 refracts such that it strikes the top surface of waveguide 305 at an angle β relative to the optical axis of waveguide 305. The angle β is defined as the internal propagation angle. The vertical distance y between the center of collimated light beam 315 and the apex of integrated lens 310 is chosen such that β is less than the complement of the critical angle allowing total internal reflection to occur. For a given radius R for the curved surface of integrated lens 310 and index of refraction n for integrated lens 310, the distance y and angle β are related by the equation:

$$y = R\left[1 - \frac{n\sin\beta}{\sqrt{1 - 2n\cos\beta + n^2}}\right]. \quad [\text{Eq. 1}]$$

Since collimated light beam 315 has a spatial extent, the curved surface of integrated lens 310 will act to focus collimated light beam 315. The radius R of the curved surface of integrated lens 310 is chosen such that for a given beam diameter of collimated light beam 315, the range of angles incident on the top surface of waveguide 305 is appropriate to provide a uniform evanescent field strength within the detection region while remaining outside the critical angle for TIR. It may be desired that collimated light beam 315 be focused on the top surface the waveguide 305 to allow for the greatest tolerance to misalignment. The total thickness t for the structure formed from waveguide 305 and integrated lens 310 that leads to a focused beam on the top surface may be given by:

$$t = R + \frac{(y-R)^3}{R^2 n^2}. \quad [\text{Eq. 2}]$$

When an appropriate thickness t is used, collimated light beam 315 will focus at a horizontal distance L from the center of the circle defining the curved surface of integrated lens 310. L may be related to the previously defined quantities by the equation:

$$L = \frac{t-y}{\tan\beta} - \sqrt{2yR - y^2}. \quad [\text{Eq. 3}]$$

The structure including waveguide 305 and integrated lens 310 may be manufactured in several different ways. One method is to have the entire assembly constructed in plastic by injection molding technology. An alternative method is to fabricate the planar waveguide and lens element separately from similar index materials. The two elements may then be joined permanently by a transparent optical cement, optical contacting, or temporarily with index matching fluid/oil/gel.

Geometries such as those described in connection with FIG. 3 easily allow the adjustment of the internal propagation angle (β) through a translation, rather than a rotation, of the incident laser beam. This allows for a less complicated mechanical design to couple the laser to the waveguide. Additionally, a new injection molded waveguide is not necessary when it is desired to change the incident angle because the focal point of the lens using the disclosed geometry of FIGS. 3 and 4 is insensitive to the translation of a laser beam relative to the optical axis of waveguide 305. Further, a desired change in the incident angle is accomplished without changing the readout instrument, allowing variation of cartridge function without physical changes in the instrument. A barcode on the cartridge may be utilized to identify information used to interpret signals from a given cartridge.

To prevent light from leaking from the waveguide 305 after the first reflection from the top surface, the cylindrical lens 310 is truncated such that it does not extend beyond the location of the focus. The area defined by the line connecting the apex of integrated lens 310 and the point on the bottom surface opposite the focus (see, e.g., 'optical deadzone 355 in FIG. 3) will never have light propagate in it that successfully couples to the waveguide. As such, the precise shape of the lens in the area designated optical deadzone 355 can be any convenient shape provided integrated lens 310 does not extend beyond the vertical line passing through the focus. For a single injection molded device where minimizing material costs is important, removing all plastic in the area labeled optical deadzone 355 may be desirable. If two separate components made through conventional optical manufacturing processes are fabricated, integrated lens 310 that has been diced to remove material beyond the focus can be easily manufactured. A material that has low autofluorescence properties may be desirable to minimize background contributions in the signal collection.

Because integrated lens 310 is used in off-axis geometry, minor optical aberrations at the focus may be exhibited if the curved surface is circular. While a circular profile functionally works, the use of an aspheric surface may be employed to extend the range of the vertical position of the incident beam for which the beam will be coupled to waveguide 305, allowing a larger range of adjustment of the angle β. The appropriate deviation from a circular profile can be calculated with optical ray tracing programs familiar to those skilled in the art.

The large area of the top surface of waveguide 305 before the focus may allow for a sample chamber to be sealed. Gasket 325 sealing surface may be absent from the optical path. Therefore, a larger range of gasket materials may be possible that only need to be evaluated for their chemical/biological compatibility and not their optical properties. For example, an adhesive backed spacer can be utilized to form a sealed flowcell without a complicated clamping mechanism. Multiple flow cells can also be incorporated into a single biosensor by utilizing a gasket with multiple channels.

Figure 6:
FIG. 6 is a cavalier projection view illustrating an exemplary gasket with multiple channels.

FIG. 6 is a cavalier projection view illustrating an exemplary gasket 605 with multiple channels. The width of each channel may be chosen to match the unfocused dimension of the incident beam such that light coupling to the gasket along the length of the waveguide is minimized. A mechanism for translating the incident beam between channels may be included. In addition, the top surface of waveguide 305 within the flow channels may be appropriately treated to allow for the capture of fluorescently labeled target molecules such as proteins, RNA, DNA, or cellular structures.

A lid attached to the gasket completes the flow cell. Fluid samples can be introduced through orifices in the lid and flow through the channels, allowing the fluid to interact with the top waveguide surface. Fluid reservoirs exterior to the flow channel can also be included to allow the introduction of fluids into the flow channel and an overflow reservoir at the outlet port of the flow channel to contain the fluid after it has passed through the flow channel. With plastic components, the gasket may be optionally eliminated by molding the channels into one of the plastic components and joining the two plastic components directly with methods known to those skilled in the art (e.g., laser or ultrasonic welding).

The evanescent field created by the light within waveguide 305 can excite fluorophores that have attached to the top surface of waveguide 305. As the fluorophores relax and emit frequency shifted radiation, the emitted light may be captured by a lens or series of lenses (e.g., collection and filtering optics 345) to transfer an image of the surface to a plane that is imaged by a light capturing device (e.g., imaging device 350) such as a CCD or CMOS sensor. An optical filter may also be placed between the waveguide surface and the imaging device to eliminate scattered incident light that has not been frequency shifted by the captured fluorophores.

Figure 7:
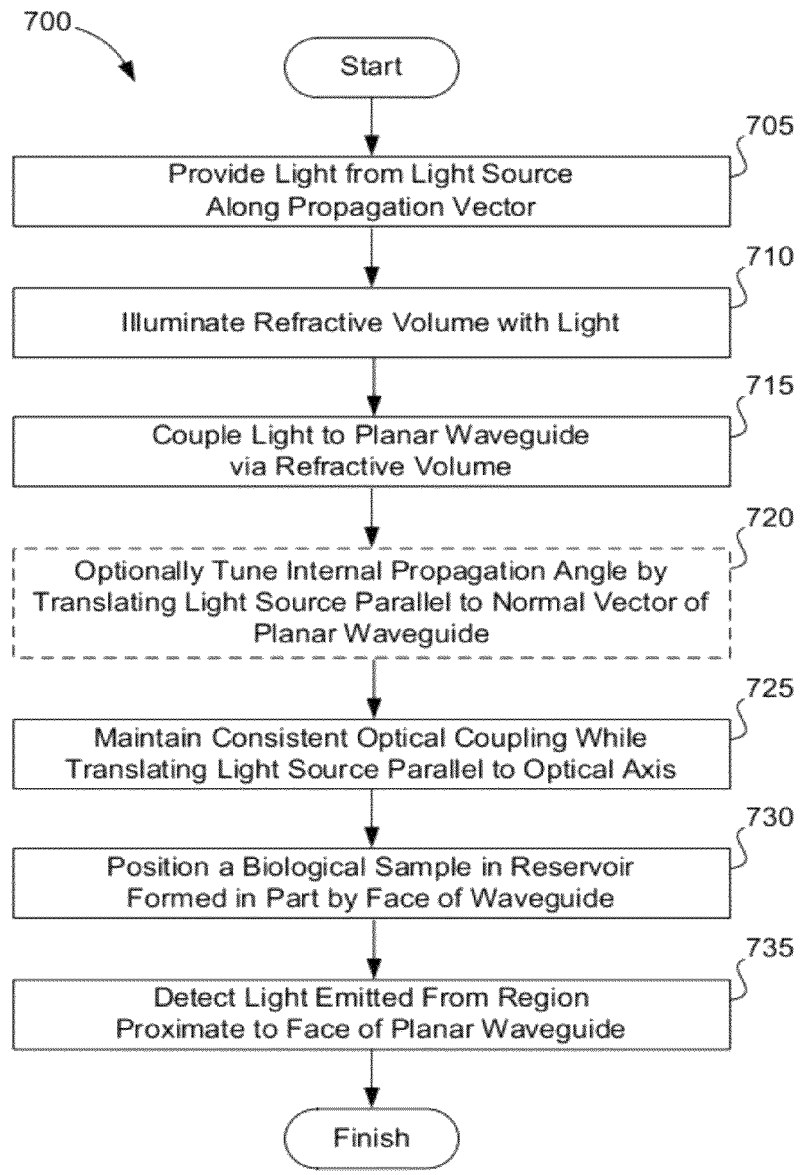
FIG. 7 is a flowchart of an exemplary method for performing sample analysis.

FIG. 7 is a flowchart of an exemplary method 700 for performing sample analysis. The steps of exemplary method 700 may be performed in varying orders. Furthermore, steps may be added or subtracted from exemplary method 700 and still fall within the scope of the present technology. The methodology illustrated in FIG. 7 may be performed for fluorescence detection and assay based on evanescent fields.

In a step 705, light is provided from a light source along a propagation vector. The light source may include a laser or any other source of collimated or near-collimated light.

In a step 710, a refractive volume is illuminated with the light. The refractive volume is positioned proximate to, and may be integrated with, a planar waveguide. In exemplary embodiments, the refractive volume may include at least a section of a plano-convex cylindrical lens, wherein the longitudinal axis of the refractive volume is oriented perpendicular to the optical axis and the normal vector of the planar waveguide.

In a step 715, the light is coupled to the planar waveguide via the refractive volume. The waveguide is oriented such that the propagation vector is perpendicular to the normal vector of the planar waveguide and offset from the planar waveguide in a direction parallel to the normal vector of the planar waveguide.

In an optional step 720, indicated by a dashed box, the optical coupling of the light provided by the light source to the planar waveguide is tuned by translating the light source in a direction parallel to the normal vector of the planar waveguide.

In a step 725, consistent optical coupling of the light provided by the light source to the planar waveguide is maintained while translating the light source parallel to the optical axis of the planar waveguide.

In a step 730, a biological sample is positioned in a reservoir formed at least in part by a face of the planar waveguide.

In a step 735, light emitted from a region proximate to a face of the planar waveguide is detected. In some embodiments, a detector is positioned to detect light emitted from a region proximate to the face of the planar waveguide having a plurality of capture molecules bound thereto.

For some applications, containment of the liquid layer within a sub-wavelength extent, as in the context of the applications described above, may be unfeasible. For instance, if the object of interest is a biological cell on the order of one to twenty microns in diameter, then a different approach to analyte illumination and light guiding is required.

Another important aspect to consider when designing optical waveguides for a practical application is the manufacturability of the waveguide, especially if the application is intended to enter volume production with cost requirements. The sensitivity to manufacturing tolerances must be evaluated as it can greatly influence the manufacturability and, in the worst case, render the design unfeasible. Likewise, the method for coupling light into the waveguide should be considered, since the light-insertion method may impact both the waveguide manufacturability and the engineering effort required to interface the waveguide with the light source. This issue is of particular concern if the light source will not be permanently affixed to the waveguide. Additionally, the interfacing complexity tends to increase as the waveguide dimensions decrease.

Although the coupling of light into micrometer-scale waveguides has been implemented in, for instance, telecommunications equipment, the engineering effort and manufacturing expenses are important factors to be considered for cost-sensitive applications outside of telecommunications. For instance, the various types of waveguides described above are generally inappropriate for mass production due to their complexity.

It would be desirable to use an optical waveguide to efficiently illuminate low-n media and/or objects embedded in such media, where the media or objects extend beyond the penetration depth of the evanescent field generated at a high-n to low-n interface. A low-n medium may be, for example, a material having an index of refraction lower than that of conventional solid materials, e.g., a refractive index less than ~1.5. An optical waveguide capable of effectively illuminating a core containing a low-index of refraction medium is described herein. It is noted that the terms "light" and "illumination" are used interchangeably herein.

Figure 8:
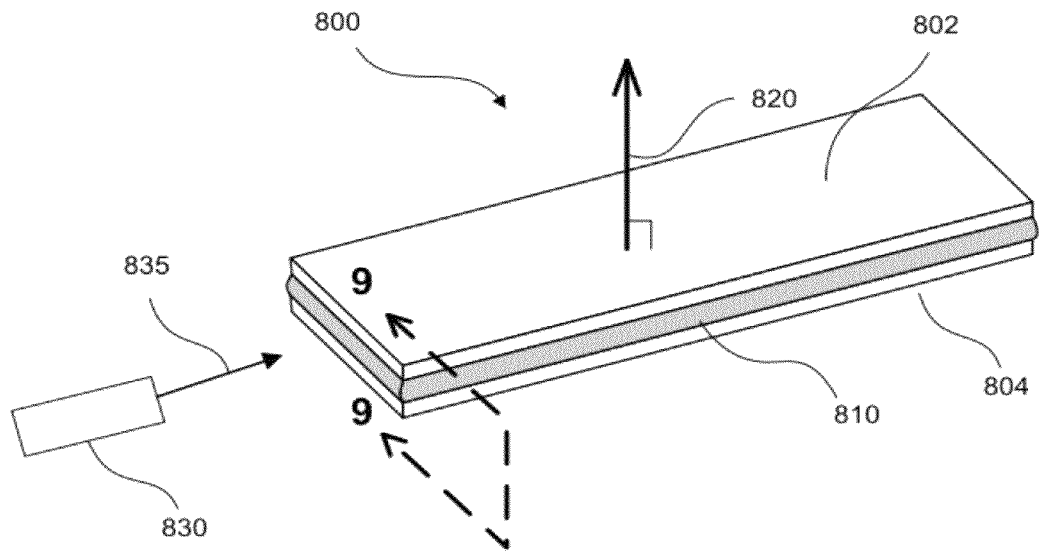
FIGS. 8 and 9 illustrate an exemplary embodiment of a planar low-n core waveguide, with liquid sample containment by two-dimensional surface tension. Within the context of the present disclosure, a planar low-n core waveguide is a planar waveguide in which the core of the waveguide exhibits a lower refractive index than the materials that surround the core.

In an embodiment, as illustrated in FIG. 8, a planar waveguide 800 includes a stack of layers formed from a first substrate 802 and a second substrate 804 sandwiching a low-n medium 810. The low-n medium is interchangeably denoted herein as the interrogation medium. First and second substrates 802 and 804 may be, for instance, optically clear so as to be transparent to light having a wavelength within a predetermined range. Low-n medium 810 is introduced between first and second substrates 802 and 804 such that first and second substrates 802 and 804 cooperate to confine low-n medium 810 therebetween. First and second substrates 802 and 804 and low-n medium 810 may have a variety of thicknesses, as long as low-n medium 810 exhibits a lower refractive index in comparison to first and second substrates 802 and 804. The present concept is compatible with numerous schemes of coupling light into the waveguide, as well as different methods of containing the low-n medium therein. The low-n medium may be liquid, gaseous and/or solid.

One-dimensional optical confinement (i.e., in a direction indicated by a surface normal 820, indicated by a thick arrow, of the first and second substrates) of light inserted into the waveguide may be provided by TIR at the interfaces between the optically clear substrates and the external surroundings. In the exemplary embodiment shown in FIG. 8, a light source 830 directs illumination 835 into planar waveguide 800 at an angle away from the substrate normal and out of the plane of the substrates such that one-dimensional optical confinement of illumination 835 is provided by planar waveguide 800 by total internal reflection at the two substrate-to-surrounding medium interfaces.

Figure 9:
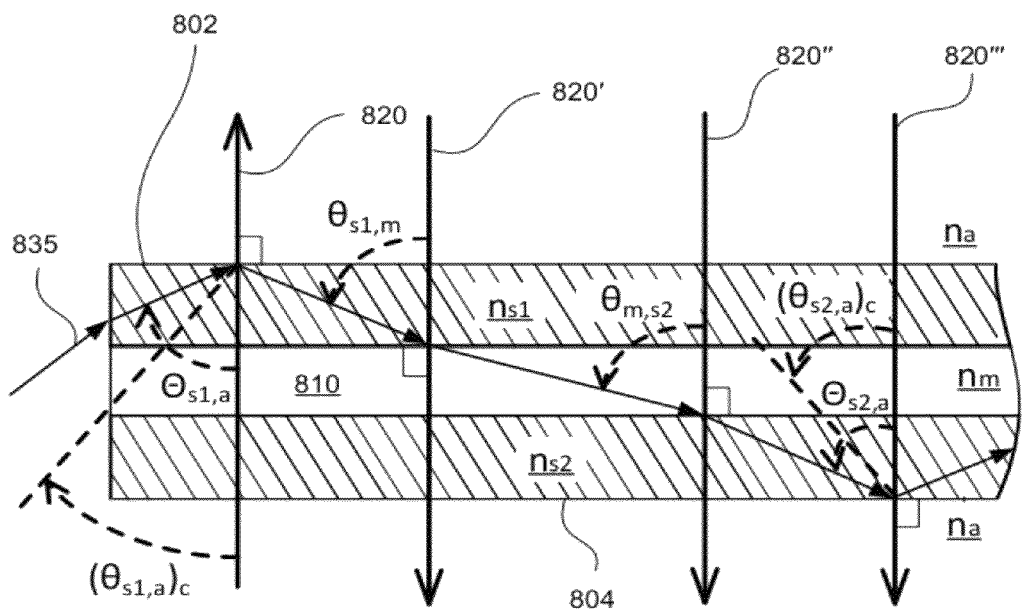

A cross-sectional view of planar waveguide 800 is shown in FIG. 9. It should be noted that the figures are not drawn to scale. As shown in FIG. 9, first substrate 802 has a refractive index $n_{s1}$, second substrate 804 has a refractive index $n_{s2}$, and low-n medium 810 has a refractive index $n_m$. Planar waveguide 800 is surrounded by air (or some other medium) with a refractive index $n_a$. The indices of refraction fulfill the requirements:

$$n_a < n_{s1}, n_{s2} \qquad \text{[Eq. 4] and}$$

$$n_a < n_m. \qquad \text{[Eq. 5]}$$

Note that critical angle for $(\theta_{1,2})_c$ for light propagation from a first material (with refractive index $n_1$) toward a second material (with refractive index $n_2$, where $n_2 < n_1$) is given by:

$$(\theta_{1,2})_c = \arcsin\left(\frac{n_2}{n_1}\right) \qquad \text{[Eq. 6]}$$

As shown in FIG. 9, light 835 enters planar waveguide 800 such that an incidence angle $\theta_{s-a}$ from first substrate 802 (with refractive index $n_{s1}$) into the surrounding medium (with refractive index $n_a$) is greater than the critical angle $(\theta_{s,a})_c$ as defined from the lower of $n_{s1}$ and $n_{s2}$, i.e., $$\theta_{s,a} > (\theta_{s,a})_c, \qquad \text{[Eq. 7]}$$

such that light 835 is contained within planar waveguide 800 by TIR. All angles are measured relative to surface normal 820. Consequently, the substrates and the interrogation medium form a multi-part waveguide, together providing light confinement in one dimension (i.e., in a direction parallel to surface normal 820). The interrogation medium can be of any type (e.g., gaseous, liquid, and biological objects embedded in a liquid) as long as the refractive index condition of Eq. 4 and incidence angle condition of Eq. 7 are satisfied.

Figure 10:
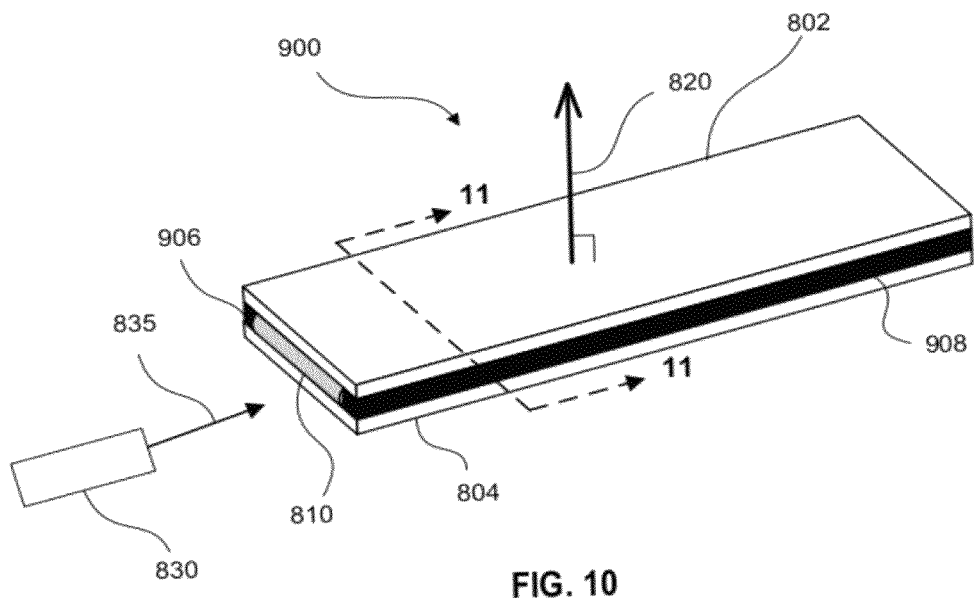
FIGS. 10 and 11 illustrate an exemplary embodiment of another planar low-n core waveguide, with sample containment by a solid sealing material for four sides and surface tension for two sides.
Figure 11:
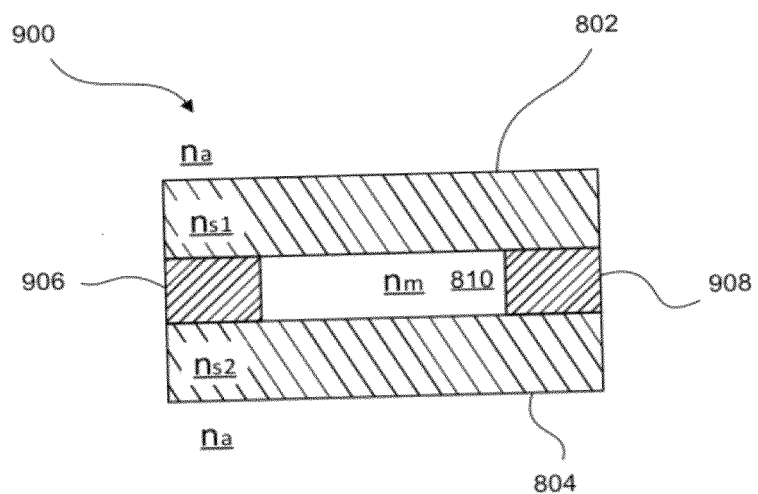

For liquid and gaseous interrogation media, the waveguide design may be modified for containing the interrogation medium. For example, in the embodiment shown in FIGS. 8 and 9, low-n medium is contained between first and second substrates 802 and 804 entirely by surface tension. FIGS. 10 and 11 show an alternative configuration for a planar waveguide 900, in which first and second substrates 802 and 804 are spaced apart by first and second gaskets 906 and 908. Still alternatively, first and second gaskets 906 and 908 may be connected to form a single contiguous gasket. It is noted that the embodiments shown in FIGS. 8-11 accommodates the addition of inlet and outlet ports (not shown) for the low-n, interrogation medium. The open ends in FIGS. 10 and 11 may be plugged using another material, thereby forming a completely-sealed volume for containing the interrogation medium.

The containment configuration should be compatible with the method for coupling light into the waveguide. For instance, the system may be configured such that the interrogation medium may be uniformly illuminated in the plane of the planar waveguide, even if the light is not solely confined within the interrogation medium. In-coupling of light 835 through the substrates is generally unaffected by the low-n medium containment schemes shown in FIGS. 8-11. Interference effects or curved interface effects (e.g., if light 835 is incident from the surrounding medium directly onto low-n medium 810, which may include an interface curvature caused by surface tension) may affect subsequent propagation of light 835 through planar waveguide 800 or 900.

Referring to FIG. 9, the illumination strength inside low-n medium 810 depends on the angle of light propagation inside planar waveguide 800. Due to the spatial compression of the light reflection at the, light propagating at angles close to the critical angle will result in greater illumination strength than light propagating at angles far from the critical angle. To a first approximation, the average illumination strength within planar waveguide 800 is inversely proportional to $\sin(\theta_{s,a})$, where $\theta_{s,a}$ is the incidence angle of propagating light at the substrate-air interface such that the light is contained within the waveguide.

Referring to FIGS. 8 and 9, the manner of coupling light into the waveguide may be chosen in accordance with the given application. For example, the incident light may be coupled into a single layer of the multi-part, planar waveguide, any combination of layers, or all layers. If the light is coupled directly into the low-n interrogation medium, for instance, the light may be inserted into the planar waveguide at any angle such that Eq. 7 is fulfilled. This range of angles include normal incidence onto the waveguide end (i.e., at an angle perpendicular to surface normal 820). On the other hand, if the light is coupled in through one of the substrates, the angle of incidence should further satisfy the conditions:

$$\theta_{s1,m} < (\theta_{s1,m})_c \qquad \text{[Eq. 8] and}$$

$$\theta_{s2,m} < (\theta_{s2,m})_c. \qquad \text{[Eq. 9]}$$

at the interfaces from first or second substrate 802 and 804 into low-n medium 810, where the subscript c denotes critical angle. Fulfillment of the appropriate one of these conditions ensures that light is eventually coupled from the substrate into the low-n medium.

A simple version of the planar low-n index waveguide may be formed from two identical substrates of a single type of material as shown in FIG. 9. Alternatively, the two substrates may be non-identical and even be composed of several disparate layers of optically-clear materials, possibly with different indices of refraction.

Note that, if first or second substrate 802 or 804 is formed of a plurality of disparate layers, the effective refractive index of the combination of the plurality of disparate layers may be expressed as $n_{eff}$, which is related to the refractive index $n_a$ of the surrounding medium by the equation:

$$n_a < n_{eff} \quad [\text{Eq. 10}]$$

Furthermore, the two substrates may be in contact with different media, such as if first substrate 802 is exposed to air while second substrate 804 is attached to a third substrate (not shown). In this case, multi-part planar waveguide 800 will still work as a waveguide as long as Eqs. 1 and 4 and the additional condition:

$$n_a < n_m, n_{eff} \quad [\text{Eq. 11}]$$

are satisfied for both substrates and surrounding media.

The angle of light propagation should be such that the incidence angle θ for the substrate-to-interrogation medium interface, as well as all interfaces between layers forming the substrate, satisfy the condition:

$$\theta < \theta_c \quad [\text{Eq. 12}]$$

and, for interfaces at the substrate and the surrounding medium, the incidence angle θ from the substrate to the surrounding medium should fulfill the condition:

$$\theta > \theta_c \quad [\text{Eq. 13}]$$

The embodiments illustrated in FIGS. 8-11 impose no constraints on the thicknesses of the interrogation medium or the two substrates as long as the refractive index and incidence angle requirements of Eqs. 1 and 4 are fulfilled. The disclosed embodiments may be particularly suitable for low-cost, volume production and may be combined with light coupling mechanisms of relatively low complexity. While planar waveguides 800 and 900 will function properly with virtually any choice of thicknesses of the interrogation medium and substrates, the actual choice of layer thicknesses may be based on a number of factors, such as the choices of materials, manufacturing methods and cost.

Figure 12:
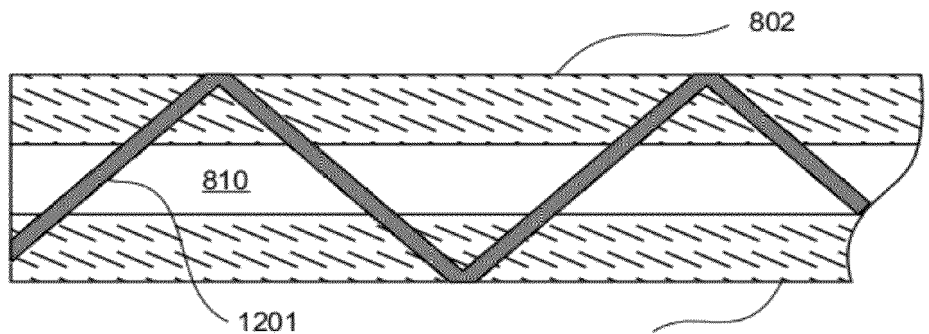
FIGS. 12-15 are illustrations of light propagating in an embodiment of a planar low-n core waveguide.
Figure 13:
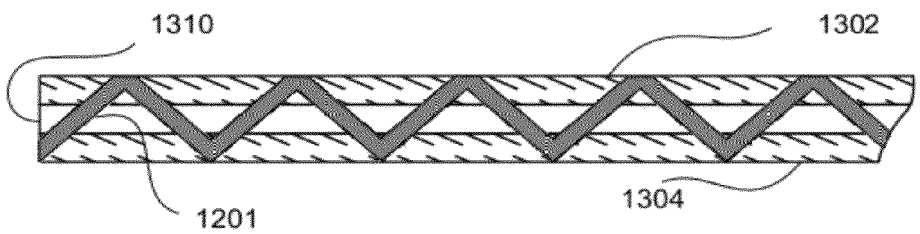
Figure 14:
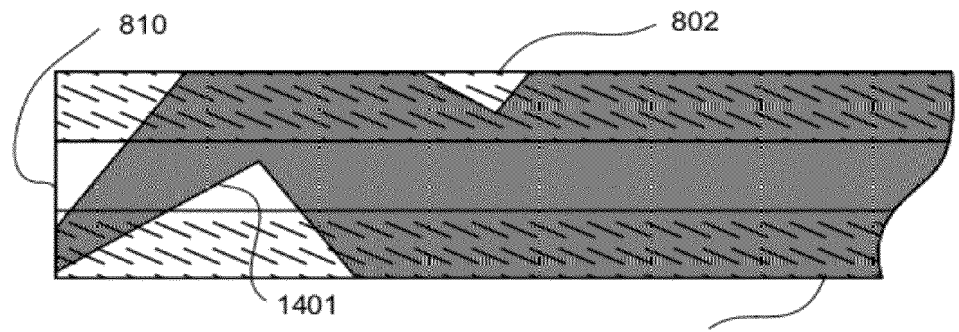
Figure 15:
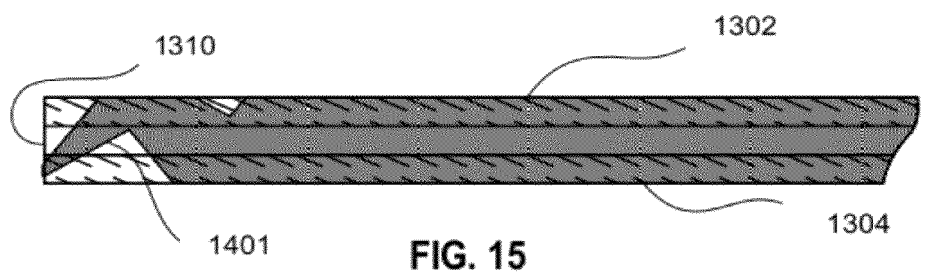

The light propagation through thick and thin versions of planar waveguide 800 is illustrated for both a collimated beam (FIGS. 12 and 13) and a diverging beam (FIGS. 14 and 15) as the light input. As shown in FIGS. 12 and 13, a collimated beam 1201 will make distinct passes through low-n medium throughout the waveguide with high intensity. For a diverging beam 1401, on the other hand, the reflected light eventually overlaps, resulting in substantially uniform illumination within the planar waveguide. Consequently, if only one or more, appropriately-placed small regions, extending no more than the portion illuminated by a single pass, require illumination, then collimated beam 1201 can provide greater intensity than diverging beam 1401 within the small region. If the intent is to illuminate a larger region, possibly in a uniform fashion, then a diverging beam 1401 may be a better choice. It should also be noted that the pairs of figures (i.e., FIGS. 12-13 and FIGS. 14-15) may be viewed as illustrations of the same planar waveguide but illuminated with collimated and diverging beams, respectively, of different beam diameters.

Efficient coupling of light into the waveguide is readily achieved with a combined waveguide thickness of macroscopic extent, e.g., on the order of few hundreds of nanometers or greater. For instance, a focused laser beam may be easily coupled into a planar waveguide of such dimensions. The mechanism for appropriately focusing the incoming light may be either integrated in the waveguide or constructed as a system separate from the waveguide. Examples of light coupling mechanisms are shown in FIGS. 16-25.

Figure 16:
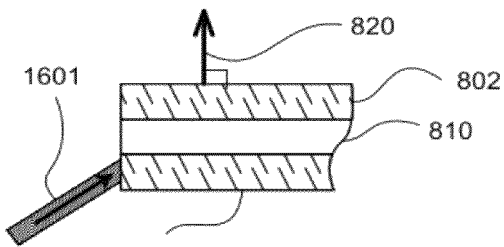
FIGS. 16-25 show diagrammatic illustrations of variations for light coupling means suitable for use with the planar low-n core waveguide.
Figure 17:
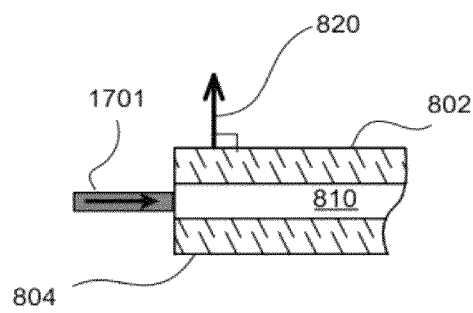
Figure 18:
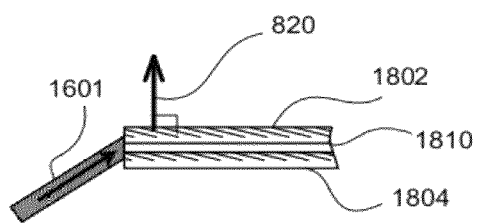
Figure 19:
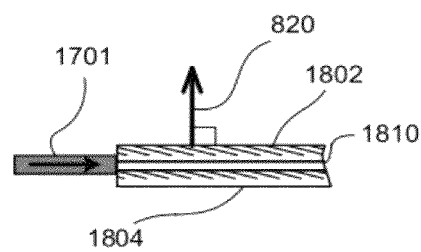

FIG. 16 shows an embodiment, in which a light beam 1601 is incident at an angle away from surface normal 820 onto second substrate 804. FIG. 17 shows a special case, in which a light beam 1701 is directly incident on low-n medium 810 at an angle perpendicular to surface normal 820. FIG. 18 shows a thin, planar waveguide embodiment, in which light beam 1601 is simultaneously incident on first and second thin substrates 1802 and 1804, respectively, and low-n medium 1810, again at an angle away from surface normal 820. FIG. 19 again shows the thin, planar waveguide formed from first and second thin substrates 1802 and 1804, respectively, and low-n medium 1810, with light beam 1701 being inserted into all three layers at an angle perpendicular to surface normal 820.

Figure 20:
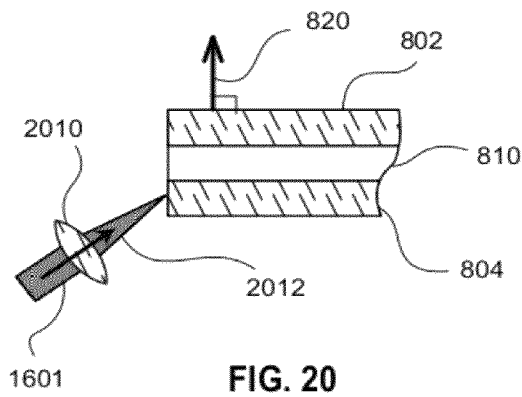
Figure 21:
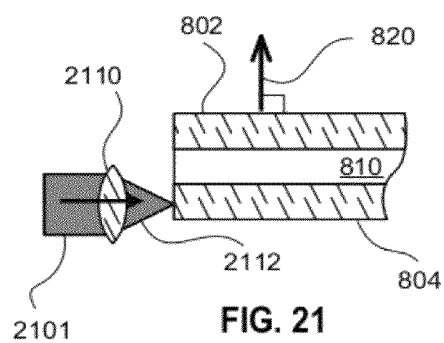

FIGS. 20 and 21 show embodiments in which an external lens is used to focus the incident light beam onto one of the two substrates. FIG. 20 shows an embodiment, in which a lens 2010 is used to focus light beam 1601 such that a focused beam 2012, which is incident from a non-normal angle away from surface normal 820, is directed into second substrate 804. Similarly, FIG. 21 shows an embodiment, in which a light beam 2101, incident at an angle perpendicular to surface normal 820, is focused by a lens 2110 to form a focused beam 2112 before being incident on second substrate 804.

Figure 22:
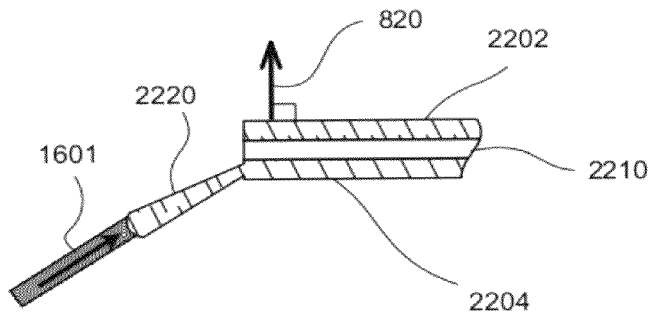
Figure 23:
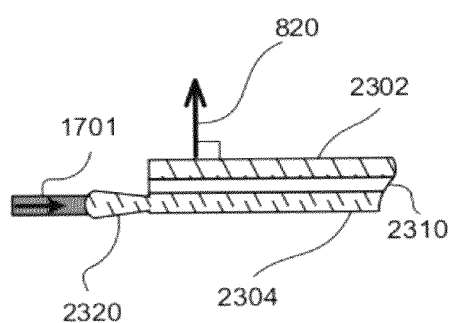
Figure 24:
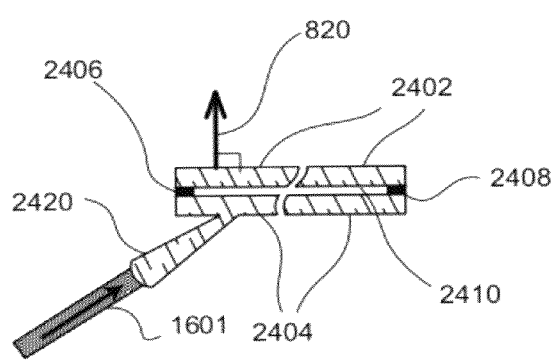
Figure 25:
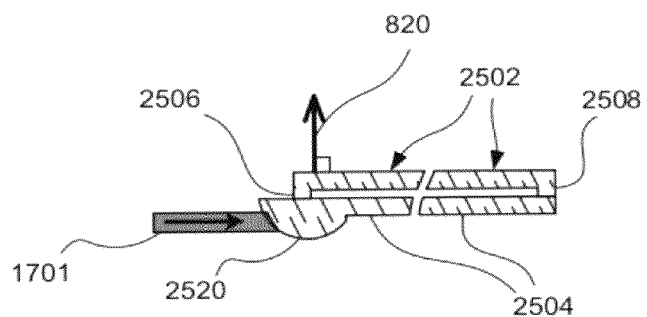

In another approach, the light may be coupled into one of the two substrates, which is equipped with an integrated lens assembly for appropriately focusing and directing the incoming light. For instance, FIG. 22 shows an embodiment, in which first and second substrates 2202 and 2204, respectively, are spaced apart to contain a low-n medium 2210 therebetween. Second substrate 2204 includes an integrated lens 2220, which is configured to receive light beam 1601 so as to couple light beam 1601 into second substrate 2204 and, subsequently, the multi-part planar waveguide configuration. FIG. 23 shows a similar embodiment, in which first and second substrates 2302 and 2304, respectively, is spaced apart to contain a low-n medium 2310 therebetween. In this embodiment, second substrate 2304 includes an integrated lens 2320, which is this time configured to receive light beam 1701, incident at an angle perpendicular to surface normal 820. Light beam 1701, received at integrated lens 2320, is directed into second substrate 2304 and, subsequently, the multi-part planar waveguide as a whole. FIG. 24 shows an alternative embodiment, which includes first and second substrates 2402 and 2404, respectively, separated by first and second gaskets 2406 and 2408, respectively, so as to contain a low-n medium 2410 therebetween. Second substrate 2404 includes an integrated lens 2420, which is configured to receive light beam 1601 at a portion of second substrate 2404 away from first gasket 2406 such that light beam 1601 is inserted into the multi-part planar waveguide structure without being blocked by first gasket 2406. Finally, FIG. 25 shows an embodiment including first and second substrates 2502 and 2504, respectively. This time, rather than including a separate gasket, first substrate 2502 includes first and second stand-offs 2506 and 2508, respectively, which are configured so as to be attachable to second substrate 2504 by, for instance, laser welding, ultrasonic welding, or other suitable bonding method. When bonded together, first and second substrates 2502 and 2504, respectively, defines a volume for containing a low-n medium 2510 therebetween. Second substrate 2504 includes an integrated lens 2520 configured for receiving light beam 1701, incident at an angle perpendicular to surface normal 820, such that light beam 1701 propagates into second substrate 2504 and, subsequently, into the multipart planar waveguide structure as a whole. Integrated lens 2520 may be, for example, an integrated lens as described in the aforementioned U.S. patent application Ser. No. 12/617, 535, such that insertion of light beam 1701 into second substrate 2504 is substantially insensitive to translation of light beam 1701 with respect to integrated lens 2520.

Figure 26:
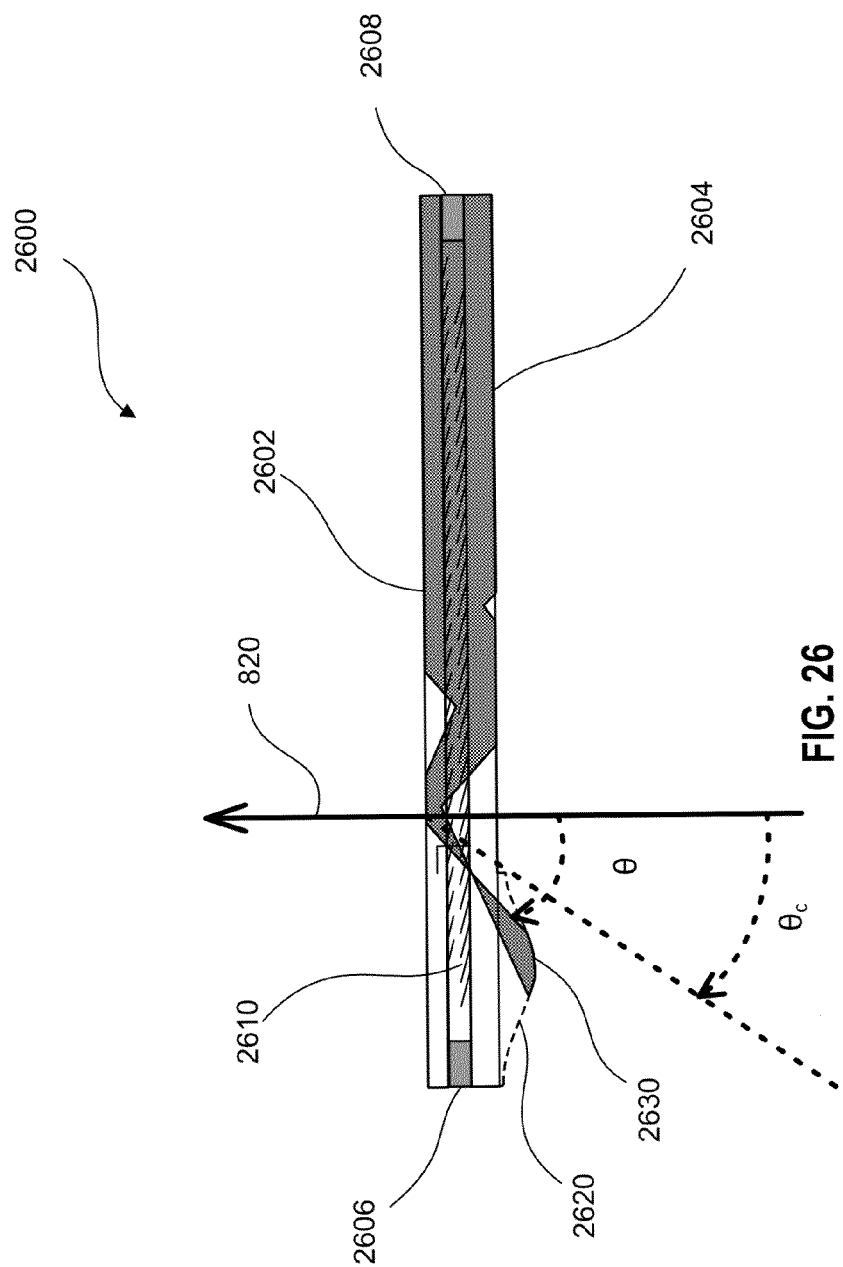
FIG. 26 shows an exemplary embodiment, in which the interrogation medium is fully contained by solid material, and the light is coupled into the waveguide itself within the containment region. The dashed line represents an exemplary shape for appropriate light coupling into the waveguide.

FIG. 26 shows a side view of an exemplary waveguide structure, shown here to illustrate insertion, propagation and containment of a light beam therethrough. A planar waveguide 2600 includes first and second substrates 2602 and 2604, respectively, spaced apart by first and second gaskets 2606 and 2608, respectively, so as to contain a low-n medium 2610 therein. Second substrate 2604 may optionally include a refractive component, such as an integrated lens 2620 (shown as a dashed curve), for facilitating insertion of a light beam 2630 into planar waveguide 2600. As shown in FIG. 26, first and second substrates 2602 and 2604, respectively, low-n medium 2610, and incident angle θ fulfill the refractive index and incident angle conditions specified in Eqs. 1 and 4 above such that, after a few TIR bounces at the substrate-air interfaces, light beam 2630 uniformly illuminates the thickness of planar waveguide 2600.

Figure 27:
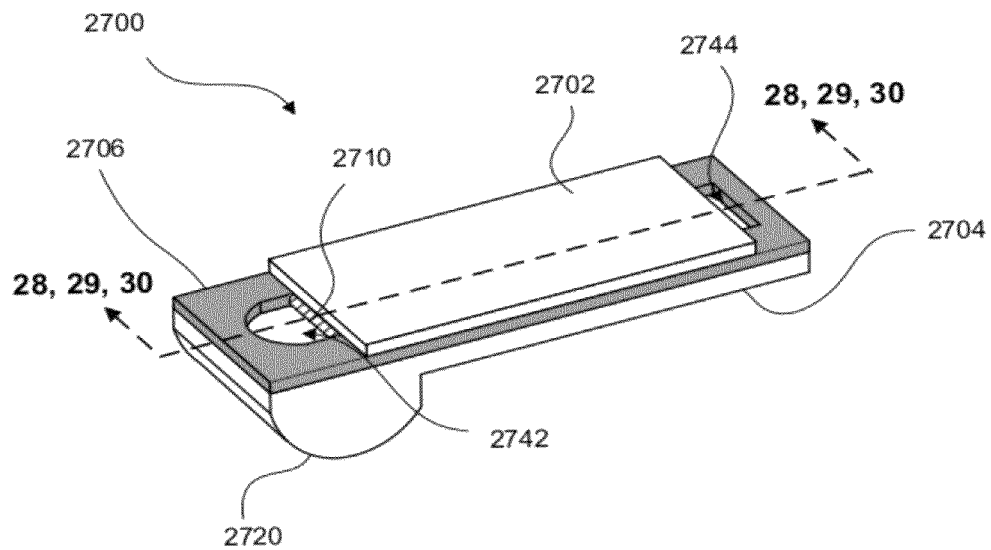
FIGS. 27-28 illustrate exemplary embodiments of a planar low-n core waveguide with a liquid interrogation medium, including light coupling means, fluid containment, and fluid inlet and outlet ports. Both substrates may be optically clear for the wavelength range of interest, as shown in FIG. 28. A gasket may be used to contain the liquid in two dimensions, as shown in FIGS. 27-28. Alternatively, the upper component may be shaped to include side walls or stand-offs, which may be directly bonded to the waveguide substrate.
Figure 28:
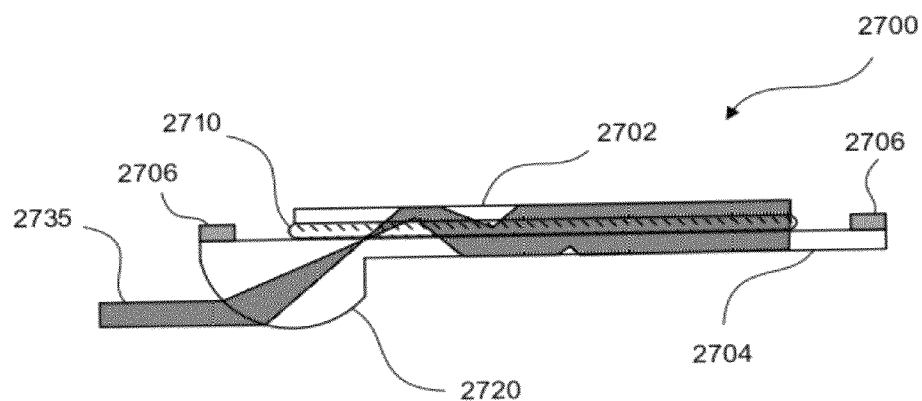

An exemplary embodiment of a cartridge system with interrogation medium containment, in- and outlet ports, and light-coupling means designed for light entry into the waveguide inside the contained region is shown in FIGS. 27-28. A waveguide cartridge 2700 includes first and second substrates 2702 and 2704, respectively, separated by a gasket 2706 so as to provide containment of a low-n medium 2710 therebetween. Second substrate 2704 includes an integrated lens 2720 for receiving light 2735 incident thereon and directing light 2735 into waveguide cartridge 2700 so that, after a few TIR bounces therein, light 2735 uniformly illuminates at least a portion of low-n medium 2710. Waveguide cartridge 2700 further includes an inlet port 2742 and an outlet port 2744, through which one or more samples may be introduced into waveguide cartridge 2700 as low-n medium 2710.

The use of optically-clear substrates may facilitate optical communication with the interrogation medium through the substrates. For instance, additional image capture through the substrates may be utilized to detect light emitted from the interrogation medium and thereby extracting information about the interrogation medium in, e.g., microscopy and/or fluorescence applications. Additionally, by using a position-sensitive detector, spatial information regarding the interrogation medium may be obtained. Alternatively, light emitted within the range of angles confined by the waveguide may be detected in the plane of the waveguide, if an appropriate pathway is established for allowing this light to exit the waveguide (not shown). For example, a mechanism for out-coupling of light may be incorporated into the substrate in a manner similar to that used for the in-coupling of light.

Figure 29:
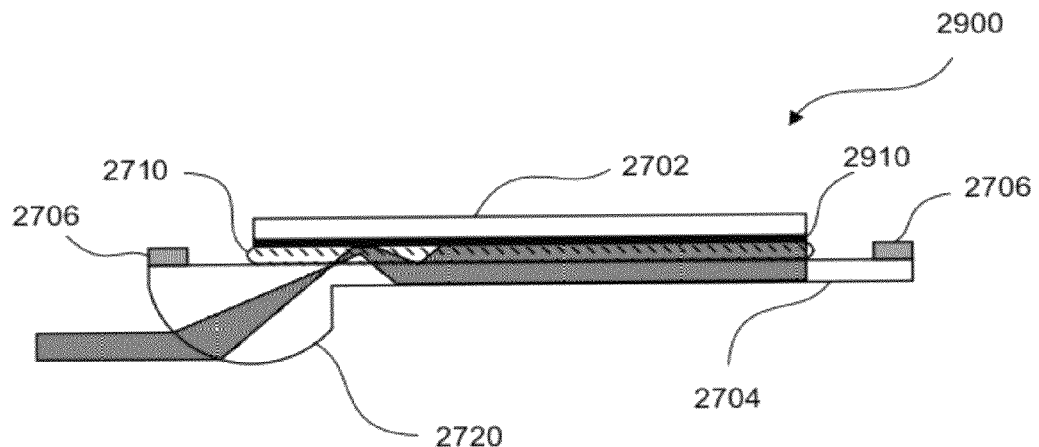
FIGS. 29 and 30 show embodiments similar to that shown in FIG. 28, wherein the upper substrate further includes a reflector.

As an alternative, one or more of the substrate-surrounding medium interfaces may be configured to be at least partially reflective. Additionally, one or more reflecting surfaces may be utilized in the waveguide. For instance, one or both of the substrate-to-interrogation medium interfaces may be configured to be partially or completely reflective in order to better contain the guided light within the interrogation medium. In the case of configurations wherein the light is coupled into the waveguide through one of the two substrates, the other one of the two substrates may be configured to include a reflective surface (e.g., at the substrate-to-interrogation medium interface), thereby increasing the illumination intensity within the interrogation medium. An example of this configuration is shown in FIG. 29, in which a waveguide cartridge 2900 further includes a reflective layer 2910 at the interface between first substrate 2702 and low-n medium 2710. The configuration as shown in FIG. 29 still allows for optical communication through second substrate 2704 (e.g., for detection of light emitted from the interrogation medium), while improving the light containment within waveguide cartridge 2900 without affecting the in-coupling of light therein. Another advantage of this configuration is a reduced distance from light entry to uniform illumination, when guiding a diverging beam. Still another example is shown in FIG. 23, in which a waveguide cartridge 2300 includes a reflective layer 2310 at the interface between the outer surface of first substrate 2702 and surrounding medium 2315. The advantages imparted in the configuration of FIG. 23 is similar to those discussed in relation to FIG. 29.

Figure 30:
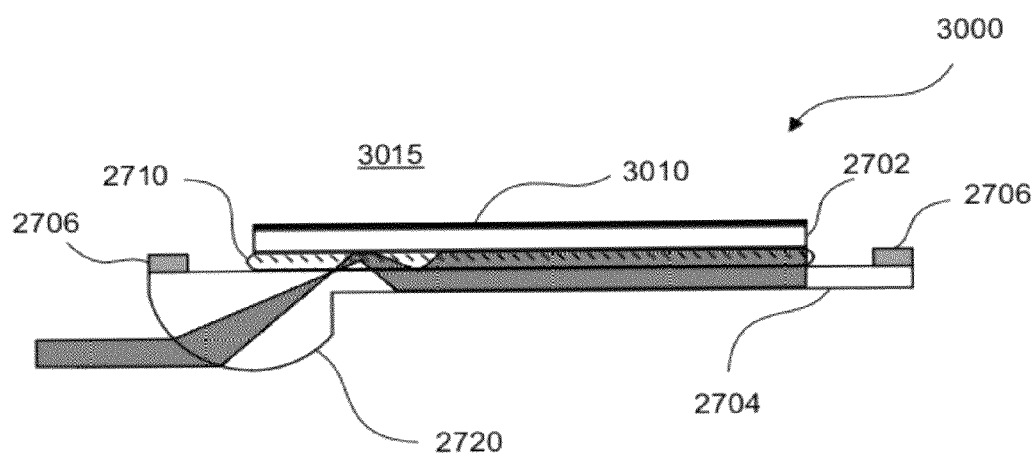

Other variations, in which one or both of the substrates include one or more reflective regions, may hold other advantages. For instance, the configuration depicted in FIG. 28 may be modified to include a reflective section located at a certain distance from the point of light entry, thereby reducing the distance required to achieve uniform illumination while maintaining means for optical communication through both substrates. Additionally, the at least partially reflective surfaces in FIGS. 29 and 30 may be used to direct light emitted by the interrogation medium (e.g., fluorescence emission) towards a detector placed underneath waveguide 100.

While each of the illustrated embodiments shows a single light beam entering the waveguide, the embodiments may be extended to accommodate multiple beams entering the waveguide. For example, the waveguide may be constructed to accept multiple beams of light by in-coupling several light beams through one port, such as a lens integrated into one of the substrates, and/or by incorporating several in-coupling ports. The beams may propagate in directions that are parallel to each other, either in co- or counter-propagating configurations, or in non-parallel configurations.

Example I

Detection of Fluorescently Labeled Human Blood Cells

Human peripheral blood mononucleocytes ("PBMCs") are labeled with CD3 Alexa Fluor 647 fluorescence stain, available from Invitrogen Corporation. The cells, whose diameter is 6-12 µm, are kept in a buffer consisting of phosphate buffered saline with 1% Bovine Serum Albumin and 0.06% sodium azide. The buffer with cells is loaded into a cartridge of the type shown in FIGS. 27 and 28. The substrate materials and the buffer lead to a critical angle at the substrate-to-interrogation medium interface of $\theta_c=61°$. 635 nm laser light is coupled into the system through the curved part of the lower substrate. The curvature is designed such that different entry heights result in different angles of incidence onto the substrate-to-interrogation medium interface. Two different laser heights were used in the present example resulting in two different angles of incidence onto the substrate-to-interrogation medium interface: (a) 57° and (b) 66°. With a laser divergence angle of 3.5° after passing through the curved surface of the lower substrate case (a) allows the light to pass through the interrogation medium and be guided by the entire cartridge as shown in FIG. 28. In case (b), on the other hand, the laser light is confined to the lower substrate and the interrogation medium is illuminated only by the evanescent field. The 635 nm laser light excites the Alexa Fluor 647 fluorophores and an imaging system positioned underneath the cartridge images fluorescence emitted from the interrogation medium.

TABLE 1

|  | Case (a) Using the low-n core waveguide configuration θ = 57° | Case (b) Evanescent illumination θ = 66° |
|---|---|---|
| # cells detected | 590 | 138 |
| Staining percentage | 56% | 13% |
| S/N for representative cell | 4.4 | 1.2 |

Raw fluorescence images (not shown) indicate that the fluorescence is strongly enhanced when the interrogation medium is directly illuminated, i.e., case (a). The results are summarized in TABLE 1. In case (a), 590 fluorescent cells are detected versus only 138 cells in case (b). The staining percentage, i.e., number of fluorescent cells divided by total number of cells, for case (a) agrees with results obtained on a flow cytometer. The signal to noise ratio, S/N, has been calculated as the peak pixel intensity of a representative cell divided by the standard deviation of the surrounding background pixel intensities. Alternatively, the signal to noise ratio could have been calculated as the peak intensity of a cell divided by the background level. However, the former method is the more appropriate parameter when concerned with the ability to distinguish a cell from the background in the images. As listed in TABLE 1, the signal to noise ratio increases almost fourfold when directly illuminating the interrogation medium.

Changes may be made in the above methods and systems without departing from the scope hereof. It should thus be noted that the matter contained in the above description or shown in the accompanying drawings should be interpreted as illustrative and not in a limiting sense. The following claims are intended to cover generic and specific features described herein, as well as statements of the scope of the present method and system, which, as a matter of language, might be said to fall therebetween.

Although each of the aforedescribed embodiments have been illustrated with various components having particular respective orientations, it should be understood that the system as described in the present disclosure may take on a variety of specific configurations with the various components being located in a variety of positions and mutual orientations and still remain within the spirit and scope of the present disclosure. For example, it should be noted that the present configuration may be applicable for systems in which the core refractive index is greater than the refractive indices of the substrates, such as if a solid core material is used, as long as the surrounding medium refractive index is less than those of the substrates. Additionally, in the various figures described above, the gasket may be eliminated and replaced with direct laser welding of first and second substrates. Furthermore, suitable equivalents may be used in place of or in addition to the various components, the function and use of such substitute or additional components being held to be familiar to those skilled in the art and are therefore regarded as falling within the scope of the present disclosure. Therefore, the present examples are to be considered as illustrative and not restrictive, and the present disclosure is not to be limited to the details given herein but may be modified within the scope of the appended claims.

What is claimed is:

1. An apparatus for illuminating a sample, the apparatus comprising:
   a waveguide including
      a first substrate including a first outer surface and a first inner surface, one of the first outer surface and the first inner surface comprising a reflective layer, and
      a second substrate including a second outer surface and a second inner surface, the first and second inner surfaces of the first and second substrates, respectively, being spaced apart from each other and partly defining a volume for confining the sample therein; and
   a light source for providing light directed toward the waveguide such that the light is optically coupled to and contained within the waveguide between the reflective layer and the second outer surface, while illuminating at least a portion of the sample confined within the volume.

2. The apparatus of claim 1, the sample containing at least one object, wherein the waveguide and the light source are configured to cooperate to uniformly illuminate the at least one object.

3. The apparatus of claim 2, wherein the at least one object is greater than one micrometer in diameter.

4. The apparatus of claim 1, further comprising a gasket for separating the first and second inner surfaces of the first and second substrates, respectively, while further defining the volume for confining the sample therein.

5. The apparatus of claim 1, wherein the light is contained at least in part by total internal reflection at the second outer surface.

6. The apparatus of claim 1, wherein the light source provides collimated light.

7. The apparatus of claim 6, further comprising a refractive element for diverging the collimated light within the planar waveguide.

8. The apparatus of claim 1, wherein the first and second surfaces are spaced apart by a distance of more than 10 microns.

9. The apparatus of claim 8, wherein the first and second surfaces are spaced apart by a distance on an order of 100 microns.

10. The apparatus of claim 1, further comprising a refractive assembly for optically coupling the light from the light source into the second substrate.

11. The apparatus of claim 10, wherein the second substrate and the refractive assembly are integrally formed from a single piece of material.

12. The apparatus of claim 11, wherein the second substrate and the refractive assembly are formed by injection molding.

13. The apparatus of claim 10, wherein the refractive assembly is configured such that a relative translation of the light source in a plane parallel to the inner surface of the second substrate is inconsequential to optical coupling of the light from the light source to the waveguide.

14. The apparatus of claim 10, a surface normal being defined as a vector perpendicular to the outer surface of the second substrate, wherein the light is incident on the refractive volume at a non-90° angle away from the surface normal.

15. A sample analysis system comprising:
   a waveguide, including
      a first substrate including a first outer surface and a first inner surface, a second substrate including a second outer surface and a second inner surface, the first and second inner surfaces of the first and second substrates, respectively, being spaced apart from each other by first and second gaskets therebetween, the gaskets and the substrates partly defining a volume for confining a sample therein, and an integrated lens configured to receive a first illumination and to insert the first illumination into the waveguide without being blocked by the gaskets;

a first light source for providing the first illumination directed toward the integrated lens such that the first illumination is contained within the waveguide between the outer surfaces of the first and second substrates while illuminating at least a portion of, the sample confined within the volume; and a detector for detecting a first light signal emitted from the sample as a result of the first illumination interacting with the portion of the sample.

16. The system of claim 15, the sample containing at least one object, wherein the waveguide and the light source are configured to cooperate to uniformly illuminate the at least one object.

17. The system of claim 16, wherein the at least one object is greater than one micrometer in diameter.

18. The system of claim 15, further comprising:
a second light source configured for providing a second illumination; and
imaging optics for directing the second illumination from the second light source to at least another portion of the sample and to the detector,
wherein the detector is further configured for detecting a second light signal resulting from the second illumination interacting with the at least another portion of the sample.

19. The system of claim 15, wherein the first illumination is contained between the outer surfaces of the first and second substrates at least in part by total internal reflection.

20. The system of claim 15, wherein the light source provides uncollimated light as the first illumination.

21. The system of claim 15, wherein at least one of the first and second outer surfaces and first and second inner surfaces is configured for at least partially reflecting light incident thereon.

22. The system of claim 21, wherein the at least one of the first and second outer surfaces and first and second inner surfaces is further configured for reflecting light of a predetermined wavelength range incident thereon.

23. The system of claim 15, further comprising a refractive assembly for optically coupling the first illumination into the second substrate.

24. The system of claim 23, wherein the second substrate and the refractive assembly are integrally formed from a single piece of material.

25. The system of claim 24, wherein the second substrate and the refractive assembly are formed by injection molding.

26. The system of claim 23, wherein the refractive assembly is configured such that a relative translation of the light source in a plane parallel to the inner surface of the second substrate is inconsequential to optical coupling of the first illumination to the planar waveguide.

27. The system of claim 23, a surface normal being defined as a vector perpendicular to the outer surface of the second substrate, wherein the first illumination is incident on the refractive volume at an angle away from the surface normal.

28. The apparatus of claim 1, the first inner surface comprising the reflective layer and the light comprising a diverging beam such that the reflective layer reduces a distance from light entry to uniform illumination along the waveguide.

29. An apparatus for illuminating a sample, the apparatus comprising:
a waveguide, including
a first substrate including a first outer surface and a first inner surface,
a second substrate including a second outer surface and a second inner surface, the first and second inner surfaces of the first and second substrates, respectively, being spaced apart from each other by first and second stand-offs therebetween, the stand-offs and the substrates defining a volume for confining a sample therein, and
an integrated lens configured to receive a light beam that is incident at an angle perpendicular to a surface normal of the first outer surface; and
a first light source for providing the light beam directed toward the integrated lens such that the light beam propagates into the second substrate and is optically coupled to and contained within the waveguide between the outer surfaces of the first and second substrates, while illuminating at least a portion of the sample confined within the volume.

* * * * *

UNITED STATES PATENT AND TRADEMARK OFFICE
CERTIFICATE OF CORRECTION

PATENT NO. : 8,331,751 B2  
APPLICATION NO. : 12/942234  
DATED : December 11, 2012  
INVENTOR(S) : Marie J. Delaney et al.

Page 1 of 1

It is certified that error appears in the above-identified patent and that said Letters Patent is hereby corrected as shown below:

In the Specification

Column 1, lines 22-25: "This research was funded in part by government support under the U.S. Department of Commerce National Institute of Standards (NIST) Advanced Technology Program (ATP), award number 70NANB7H7053. The Government has certain rights in this invention."

should read --This invention was made with government support under award number 70NANB7H7053 awarded by the U.S. Department of Commerce National Institute of Standards (NIST) Advanced Technology Program (ATP). The Government has certain rights in the invention.--

Signed and Sealed this  
Eighteenth Day of February, 2014

Michelle K. Lee  
*Deputy Director of the United States Patent and Trademark Office*